(12) United States Patent
O'Neil et al.

(10) Patent No.: US 8,829,058 B2
(45) Date of Patent: Sep. 9, 2014

(54) COMPOUNDS AND METHOD FOR REDUCING URIC ACID

(75) Inventors: James Dennen O'Neil, Frederick, MD (US); Michael K. Bamat, Potomac, MD (US); Reid W. von Borstel, Potomac, MD (US); Shalini Sharma, Gaithersburg, MD (US); Ramachandran Arudchandran, Germantown, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 407 days.

(21) Appl. No.: 12/920,555

(22) PCT Filed: Mar. 13, 2009

(86) PCT No.: PCT/US2009/037128
§ 371 (c)(1),
(2), (4) Date: Sep. 1, 2010

(87) PCT Pub. No.: WO2009/151695
PCT Pub. Date: Dec. 17, 2009

(65) Prior Publication Data
US 2011/0014176 A1    Jan. 20, 2011

Related U.S. Application Data

(60) Provisional application No. 61/036,294, filed on Mar. 13, 2008.

(51) Int. Cl.
| | | |
|---|---|---|
| A01N 31/14 | (2006.01) | |
| A61K 31/075 | (2006.01) | |
| A01N 35/00 | (2006.01) | |
| A61K 31/12 | (2006.01) | |
| A01N 31/08 | (2006.01) | |
| A61K 31/05 | (2006.01) | |
| A01N 37/10 | (2006.01) | |
| A61K 31/195 | (2006.01) | |

(52) U.S. Cl.
USPC ............ 514/721; 514/568; 514/679; 514/736

(58) Field of Classification Search
None
See application file for complete search history.

(56) References Cited

U.S. PATENT DOCUMENTS

| | | | |
|---|---|---|---|
| 6,677,473 B1 | 1/2004 | Madison et al. | |
| 6,858,602 B2 | 2/2005 | Sharma et al. | |
| 6,916,848 B2 | 7/2005 | Sharma | |
| 6,924,314 B2 | 8/2005 | Sharma et al. | |
| 6,946,491 B2 | 9/2005 | Sharma et al. | |
| 7,012,071 B2 | 3/2006 | Sharma et al. | |
| 7,041,659 B2 | 5/2006 | Sharma | |
| 7,045,541 B2 | 5/2006 | Sharma | |
| 7,101,910 B2 | 9/2006 | Sharma et al. | |

(Continued)

FOREIGN PATENT DOCUMENTS

| | | |
|---|---|---|
| EP | 1820515 A1 | 8/2007 |
| WO | 02100341 A2 | 12/2002 |

(Continued)

OTHER PUBLICATIONS

Arnoldi, et al., "Synthesis of 3-Aryl-1,4-benzoxathianes: Application to the preparation of a sweet compound", Journal of the Chemical Society, Perkin Transactions, 1:1241-1244, 1994.

(Continued)

Primary Examiner — James D Anderson
Assistant Examiner — Stephanie Springer
(74) Attorney, Agent, or Firm — Lewis J. Kreisler

(57) ABSTRACT

Uric acid in mammalian subjects is reduced and excretion of uric acid is increased by administering a compound of Formula I or a pharmaceutically acceptable salt thereof.

(I)

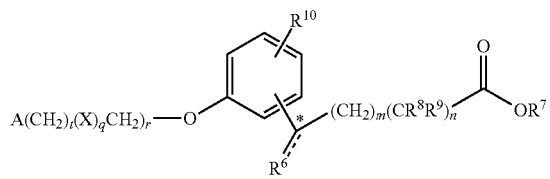

In Formula I m is 0, 1, 2, 3 or 4; n is 0 or 1; t is 0 or 1; q is 0 or 1; and r is 0, 1 or 2. $R^6$ is hydrogen, O or hydroxyl. $R^7$ is hydrogen or alkyl having from 1 to 3 carbon atoms. One of $R^8$ and $R^9$ is alkyl having from 1 to 3 carbon atoms, and the other is hydrogen or alkyl having from 1 to 3 carbon atoms. $R^{10}$ is hydrogen, halo, alkyl having from 1 to 3 carbon atoms or alkoxy having from 1 to 3 carbon atoms. X is C(O) and r is 0 and t is 0; or X is $NH(R^{11})$ wherein $R^{11}$ is hydrogen or alkyl having from 1 to 3 carbon atoms. A is phenyl, unsubstituted or substituted by 1 or 2 groups selected from halo, hydroxy, methyl, ethyl, perfluoromethyl, methoxy, ethoxy, and perfluoromethoxy; or a 5 or 6 membered heteroaromatic ring having 1 or 2 ring heteroatoms selected from N, S and O and the heteroaromatic ring is covalently bound to the remainder of the compound of Formula I by a ring carbon; or cycloalkyl having from 3 to 6 ring carbon atoms wherein the cycloalkyl is unsubstituted or one or two ring carbons are independently monosubstituted by methyl or ethyl. The uric acid-lowering effects of the Compounds of Formula I are used to treat or prevent a variety of conditions including gout, hyperuricemia, elevated levels of uric acid that do not meet the levels customarily justifying a diagnosis of hyperuricemia, renal dysfunction, kidney stones, cardiovascular disease, risk for developing cardiovascular disease, tumor-lysis syndrome, and cognitive impairment.

10 Claims, 3 Drawing Sheets

(56) References Cited

U.S. PATENT DOCUMENTS

| | | | |
|---|---|---|---|
| 7,323,480 B2 | 1/2008 | Zhu et al. |
| 7,329,782 B2 | 2/2008 | Sharma |
| 7,494,537 B2 | 2/2009 | Ono et al. |
| 7,514,555 B2 | 4/2009 | Hodge et al. |
| 7,547,802 B2 | 6/2009 | Sharma |
| 7,605,181 B2 | 10/2009 | Hodge et al. |
| 7,615,575 B2 | 11/2009 | Hodge et al. |
| 7,622,491 B2 | 11/2009 | Zhu et al. |
| 7,645,772 B2 | 1/2010 | Hodge et al. |
| 7,851,494 B2 | 12/2010 | Sharma et al. |
| 7,863,475 B2 | 1/2011 | Sharma |
| 2003/0220399 A1 | 11/2003 | Luskey et al. |
| 2005/0090555 A1 | 4/2005 | Sharma et al. |
| 2007/0010670 A1 | 1/2007 | Hirate et al. |
| 2007/0099846 A1 | 5/2007 | Chang |
| 2007/0105958 A1 | 5/2007 | Sharma et al. |
| 2007/0197512 A1 | 8/2007 | Inoue et al. |
| 2007/0197650 A1 | 8/2007 | Coop et al. |
| 2007/0244172 A1 | 10/2007 | Sharma et al. |
| 2008/0015254 A1 | 1/2008 | Hodge et al. |

FOREIGN PATENT DOCUMENTS

| | | |
|---|---|---|
| WO | 2004041165 A2 | 5/2004 |
| WO | 2004073611 A2 | 9/2004 |
| WO | 2004091486 A2 | 10/2004 |
| WO | 2004098496 A2 | 11/2004 |
| WO | 2007056771 A2 | 5/2007 |
| WO | 2007087506 A2 | 8/2007 |
| WO | 2007146768 A2 | 12/2007 |
| WO | 2009091732 A1 | 7/2009 |

OTHER PUBLICATIONS

Kappe, et al., Synthes of potentieller metaboliten of 2-amino-N-(β-hydroxy-2,5-dinnethoxyphenethyl)-acetamids (Midodrin), Archiv der Pharmazie (Weinheim, Germany), 308(5):339-346, 1975. (German language).

Accession No. 83:178502 corresponding to Kappe, et al., Synthesis of potential metabolites of 2-amino-N-(β-hydroxy-2,5-dimethoxyphenethyl)acetamide (Midodrine), Archiv der Pharmazie (Weinheim, Germany), 308(5):339-346, 1975.

Brown, et al., "Use of ethoxy-homologs as internal standards for determination of urinary vanillylmandelic acid and normetanephrine in man by high performance liquid chromatography", Journal of Liquid Chromatography, 9(4): 831-843,1986.

Ciofi-Baffoni, et al, "Synthesis of oligomeric mimics of lignin", Journal of the Chemical Society, Perkin Transactions, Organic and Bio-Organic Chemistry, 1: 3207-3218, 1998.

Benigni, et al., Synthesis of two new metabolites of catecholamines: 3,4-dihydroxyphenylethylene glycol and 4-hydroxy-3-methoxyphenylethyleneglycol, Journal of Medicinal Chemistry, 6(5):.607-608, 1963.

Armstrong, K.A. et al., "Does Uric Acid Have a Pathogenetic Role in Graft Dysfunction and Hypertension in Renal Transplant Patients?," Transplantation, 80(11):1565-1571 (2005).

Avaram, V., and E. Krishnan, "Hyperuricemia—Where Nephrology Meets Rheumatology," Rheumatology (Oxford), 47(7): 960-964, (2008).

Bainbridge. S.A. and Roberts, J.M., "Uric Acid as a Pathogenic Factor in Preeclampsia," Placenta 29, Supplement A, Trophoblast Research, vol. 22: S67-S72, (2008).

Bos et al., "Uric Acid is a Risk Factor for Myocardial Infarction and Stroke: the Rotterdam Study," Stroke. 37(6): 1503-7 (Jun. 2006).

Cengel A., et al., "Serum uric Acid Levels as a Predictor of In-hospital Death in Patients Hospitalized for Decompensated Heart Failure," Acta Cardiol, 60(5): 489-492, (Oct. 2005).

Chien, K-L, et al., "Plasma Uric Acid and the Risk of Type 2 Diabetes in a Chinese Community," Clin. Chem. 54(2): 310-316, (2008).

Cirillo et al., "Uric Acid. The Metabolic Syndrome, and Renal Disease," J Am Soc Nephrol. 17:S165-8, (2006).

Coutinho et al "Associations of Serum Uric Acid with Markers of Inflammation, Metabolic Syndrome. and Subclinical Coronary Atherosclerosis," Amer. J. Hypertens, 20: 83-89 (2007).

Feig, D.I., and Johnson, R.J., "The Role of Uric Acid in Pediatric Hypertension," J Ren Nutrition 17(1): 79-83. (2007).

Feig, D.I., et al., "Effect of Allopurinol on Blood Pressure of Adolescents With Newly Diagnosed Essential Hypertension" JAMA 300(8): 924-932.( 2008).

Halevy et al., "Allopurinol is the Most Common Cause of Stevens-Johnson Syndrome and Toxic Epidermal Necrolysis in Europe and Israel," J Am Acad Dermatol. 58(1):25-32, (2008).

Inokuchi, T., et al., "Plasma IL-18 and Other Inflammatory Cytokines in Patients With Gouty Arthritis and Monosodium Urate Monohydrate Crystal-Induced Secretion of IL-18," Cytokine. 33(1): 21-27, (2006).

Ioachimescu, A.G. et al. "Serum Uric Acid, Mortality and Glucose Control in Patients With Type 2 Diabetes Mellitus: a Precis Database Study," Diabet. Med. 24 (12) 1369-1374 (2007).

Ishizaka, N., et al., "Association Between Vasc Uric Acid, Metabolic Syndrome, and Carotid Atherosclerosis in Japanese Individuals," Arterioscler Thromb Vasc Biol., 25: 1038-44. (2005).

Jee, S.A., et al. "Serum Uric Acid and Risk of Death From Cancer. Cardiovascular Disease or All Causes in Men," Eur. J. Cardiovascular Prev. Rehab., 11(3):185-191, (2004).

Kanellis, J., and Kang, D-H., "Uric Acid as a Mediator of Endothelial Dysfunction, Inflammation, and Vascular Disease," Semin Nephrol., 25(1); 39-42. (2005).

Kang, D-H., et al., "Uric Acid Causes Vascular Smooth Muscle Cell Proliferation by Entering Cells Via a Functional Urate Transporter," Am J Nephrol. 2005 25(5):425-33 (2005).

Khosla, UM, et al., "Hyperuricemia Induces Endothelial Dysfunction," Kidney Int. 67(5):1739-42, (2005).

Krishnan, E., et al. "Gout in Ambulatory Care Settings in the United States," Journal of Rheumatology, 35(3): 498-501 (2008).

Lehto, S., et al., "Serum Uric Acid is a Strong Predictor of Stroke in Patients With Non-Insulin Dependent Diabetes Mellitus," Stroke 29: 635-639(1998).

Leyva, F. et al., "Uric Acid in Chronic Heart Failure: A Marker of Chronic Inflammation", Eur. Heart J. 19(12): 1814-1822, (1998).

Mikuls, T.R., et al. "Gout Epidemiology; Results from the UK General Practice Research Database, 1990-1999." Annals of the Rheumatic Diseases, 64:267-272, (2005).

Pascual-Figal, D.A., et al., "Hyperuricaemia and Long-Term Outcome After Hospital Discharge in Acute Heart Failure Patients," Eur J Heart Fail., 9:518-524, (2007).

Perlstein, T.S., et al., "Uric Acid and the State of the Intrarenal Renin-Angiotensin System in Humans," Kidney International. 66: 1465-1470, (2004).

Perry. I.J. et al., "Prospective Study of Risk Factors for Development of Non-Insulin Dependent Diabetes in Middle Aged British Men," BMJ, 310 (6979) 560-564, (1995).

Price, K.L., et al., "Human Vascular Smooth Muscle Cells Express a Urate Transporter," J Am Soc Nephrol. 17(7): 1791-1795, (2006).

Reidel, A. A., et al. "Compliance with Allopurinol Therapy Among Managed Care Enrollees with Gout: A Retrospective Analysis of Administrative Claims," Journal of Rheumatology, 31:1575-1581, (2004).

Ruggiero, C., et al., "Uric Acid and Inflammatory Markers," European Heat Journal, 27: 1174-1181, (2006).

Saito, et al., "Tissue Hypoxia in Sleep Apnea Syndrome Assessed by Uric Acid and Adenosine," Chest, 122: 1686-1694, (2002).

Sautin, Y.Y., et al., "Adverse Effects of the Classic Antioxidant Uric Acid in Adipocytes: NADPH Oxidase-Mediated Oxidative/Nitrosative Stress," Am. J. Physiol. Cell Physiol., 293: C584-0596, (2007).

Schretlen. DJ. et al., "Serum Uric Acid and Cognitive Function in Community-Dwelling Older Adults", Neuropsychology, 21(1): 136-140, (Jan. 2007).

Shankar, A. et al., "Association Between Serum Uric Acid Level and Peripheral Artery Disease," Atherosclerosis, doi 10: 1016, (Epub 2007), vol. 196(2): 74-755 (2008).

Stamp, L., et al. "Gout in Solid Organ Transplantation: A Challenging Clinical Problem", Drugs, 65(18):2593-2611, (2005).

(56) References Cited

OTHER PUBLICATIONS

Strasak. AM et al., "Serum Uric Acid and Risk of Cancer Mortality in a Large Prospective Male Cohort," Cancer Causes Control, 18(9): 1021-1029, (2007).

Strasak, AM et al., "The Role of Serum Uric Acid as an Antioxidant Protecting Against Cancer: Prospective Study in More Than 28,000 Older Austrian Women," Annals Oncol., 18(11): 1893-1897, (2007).

Strasak. A.M. et al., "Serum Uric Acid and Risk of Cardiovascular Mortality; A Prospective, Long-Term Study of 83,683 Austrian Men," Clin Chem. 54 (2) 273-284, (2008).

Sundström, J., et al., "Relations of Serum Uric Acid to Longitudinal Blood Pressure Tracking and Hypertension Incidence," Hypertension, 45(1):28-33, (2005).

Syamala, S. et al. "Association Between Serum Uric Acid and Prehypertension Among US Adults," J. Hypertens., 25(8): 1583-1589. (2007).

Tseng, CH, "Independent Association of Uric Acid Levels With Peripheral Artery Disease in Taiwanese Patients With Type 2 Diabetes." Diabet. Med., 21(7):724-729, (2004).

Verhulst, S.L., et al., "Sleep-Disordered Breathing and Uric Acid in Overweight and Obese Children and Adolescents," Chest, 132: 76-80, (2007).

Wallace, K. L., et al., "Increasing Prevalence of Gout and Hyperuricemia over 10 Years Among Older Adults in a Managed Care Population," Journal of Rheumatology, 31:1582-1587, (2004).

Watanabe, S., et al. "Cerebral Oxidative Stress and Mitochondrial Dysfunction in Oxonate-Induced Hyperuricemie Mice", J. Health Science, 52(6): 730-737, (2006).

Yamamoto, Y., et al "Allopurinol Reduces Neointimal Hyperplasia in the Carotid Artery Ligation Model in Spontaneously Hypertensive Rats," Hypetens. Res, 29(11): 915-921, (2006).

Zoccali, C., et al., "Uric Acid and Endothelial Dysfunction in Essential Hypertension," J Am Soc Nephroi., 17(5): 1466-71, (2006).

Pending (as of Oct. 26, 2010) Claims from U.S. Appl. No. 12/989,724.

Allowed (as of Dec. 6, 2010) Claims from U.S. Appl. No. 12/550,482.

Bieber, et al., "Gout: On the Brink of Novel Therapeutic Options for an Ancient Disease", Arthritis & Rheumatism, 50 (8): 2400-2414, Aug. 2004.

Anzai, et al., "The Multivalent PDZ Domain-containing Protein PDZK1 Regulates Transport Activity of Renal Urate-Anion Exchanger URAT1 via Its C Terminus", J. Biol. Chem., 279(44): 45942-45950, 2004.

Фармакология: учебник для ВУЗов, под ред. Р.Н. Аляутдина, 2-е издание, исправленное, М. ГЭОТАР-МЕД, 2004 (in Russian only); Farmakologjia: uchebnik dlja VUZov, pod red. R.N. Aljautdin, 2-e izdanie, ispravlennoe, M. GJeOTAR-MED, 2004.

COMPOUNDS AND METHOD FOR REDUCING URIC ACID

BACKGROUND OF THE INVENTION

Diseases caused by elevated levels of uric acid fall into two major categories: disorders caused by precipitation of uric acid crystals and diseases related to pathological effects of soluble uric acid. Gouty arthritis is the classic example of the former. Deposition of urate crystals in the kidney is also a common cause of renal dysfunction.

Gout is most commonly manifested as inflammation of one or more of the joints in the body resulting in mild to severe pain. These events may be episodic and/or chronic. Over time gout can result in the destruction of cartilage and bone, development of uric acid crystal deposits, kidney pain and dysfunction as well as kidney stones. Gout can affect other organs as well.

Gout is caused by hyperuricemia and the consequent formation and deposition of uric acid crystals in tissues, joints, kidneys and other organs. The uric acid comes from normal cell metabolism and from some types of foods and beverages. The excessive levels of uric acid are the result of too much uric acid production, impaired clearance by the kidneys (or a combination of excess production and impaired clearance), and also by some forms of medications taken for other health conditions. (Examples include diuretics, pyrazinamide, cyclosporine, low-dose aspirin, nicotinic acid and levodopa.). Many types of health conditions can also contribute to hyperuricemia and gout, including alcoholism, leukemia, lymphoma, lung cancer, tumor-lysis syndrome, smoking, psoriasis, obesity, kidney dysfunction, congestive heart failure, starvation, anemia, high blood pressure, diabetes, immobility, Lesch-Nyhan Syndrome, Down syndrome, and thyroid and parathyroid dysfunctions.

Gout is generally divided into four categories based upon progressively more severe symptoms:
1) Asymptomatic. Elevated uric acid levels in the blood, but no overt symptoms.
2) Acute gouty arthritis: Sudden onset of symptoms, often in a single joint (commonly a big toe), and then involving other joints. Symptoms include pain, swelling, redness and fever.
3) Intercritical gout: Asymptomatic phases between gout attacks.
4) Chronic tophaceous gout: A chronic condition that may include frequent attacks, constant mild pain and inflammation of joints, destruction of cartilage and bone, development of uric acid crystal deposits, kidney dysfunction and kidney stones.

Medications currently used to treat the acute symptoms of gout include nonsteroidal anti-inflammatory drugs, colchicine and corticosteroids. All of these medications can produce mild to severe side effects.

Other types of medication are used in order to try to reduce the incidence or severity of future attacks by reducing levels of uric acid. The three principal classes of medication are xanthine oxidase inhibitors (for example, allopurinol), which reduce production of uric acid from xanthine; uricosuric agents (for example, sulfinpyrazone, probenecid, benzbromarone and losartan), which are intended to improve excretion of uric acid by inhibiting reuptake of secreted uric acid in the renal tubules via inhibition of uric acid transporter 1 (URAT1) (See also US Patent Application Publication No. 2007/0010670, published Jan. 11, 2007 (Japan Tobacco Inc.)) or other elements of uric acid reuptake; and uricases, for example a pegylated-uricase such as PURICASE (Savient's pegylated recombinant mammalian uricase). These medications also often result in significant and undesirable side effects. For example, allopurinol has been reported to cause at least 100 cases of Stevens-Johnson/Toxic Epidermal Necrolysis and approximately 30 deaths each year in Europe (Halevy et al., Allopurinol is the most common cause of Stevens-Johnson syndrome and toxic epidermal necrolysis in Europe and Israel. J Am Acad Dermatol. 58(1):25-32, 2008). Probenicid and benzbromarone have been taken off the market in a number of countries due to undesirable side effects, such as liver failure in the case of benzbromarone. Patient compliance in taking these drugs is reportedly very poor (A. A. Reidel et al. "Compliance with Allopurinol Therapy among Managed Care Enrollees with Gout: A Retrospective Analysis of Administrative Claims." Journal of Rheumatology 2004; 31:1575-1581), presumably because of the side effects and/or lack of benefit.

More than 5 million people in the U.S. have gout (National Health and Nutrition Examination Survey 111, 1988-1994). The prevalence of hyperuricemia and gout in the U.S. in 1999 was reported to be 41 per 1,000 and 14 per 1,000 in the U.K. (T. R. Mikuls et al., "Gout Epidemiology: Results for the UK General Practice Research Database, 1990-1999." Annals of the Rheumatic Diseases 2005; 64:267-272). Subsequent reports indicate that the prevalence in the U.S., U.K. and other countries has been climbing steadily. (K. L. Wallace et al., "Increasing Prevalence of Gout and Hyperuricemia over 10 Years Among Older Adults in a Managed Care Population." Journal of Rheumatology 2004; 31: 1582-1587).

Hyperuricemia and gout are particularly significant issues in organ transplant recipients (Stamp, L., et al, "Gout in solid organ transplantation: a challenging clinical problem", Drugs (2005) 65(18): 2593-2611). Uric acid is often elevated in patients with renal transplants, and common immunosupressive drugs such as cyclosporine can cause particularly severe hyperuricemia. In transplant patients, allopurinol is contraindicated due to interactions with some immunosupressants such as azathioprine, and due to bone marrow failure caused by the combination. Furthermore, elevated uric acid may contribute to graft failure (Armstrong, K. A. et al., "Does Uric Acid Have a Pathogenetic Role in Graft Dysfunction and Hypertension in Renal Transplant Patients?" Transplantation (2005) 80(11): 1565-1571). Therefore, there is a particularly acute need for safe agents that reduce hyperuricemia in transplant recipients.

Diseases related to elevated soluble uric acid often involve vascular problems: hypertension (Sundstrom et al., Relations of serum uric acid to longitudinal blood pressure tracking and hypertension incidence. Hypertension. 45(1):28-33, 2005), prehypertension (Syamela, S. et al., Association between serum uric acid and prehypertension among US adults. J Hypertens. 25 (8) 1583-1589, (2007), atherosclerosis (Ishizaka et al., Association between serum uric acid, metabolic syndrome, and carotid atherosclerosis in Japanese individuals. Arterioscler Thromb Vasc Biol. (5):1038-44, 2005), peripheral artery disease (Shankar, A. et al., Association between serum uric acid level and peripheral artery disease. Atherosclerosis doi 10: 1016, 2007), vascular inflammation (Zoccali et al., Uric acid and endothelial dysfunction in essential hypertension. J Am Soc Nephrol. 17(5):1466-71, 2006), heart failure (Strasak, A. M. et al., Serum uric acid and risk of cardiovascular mortality: A prospective, long-term study of 83,683 Austrian men, Clin Chem. 54 (2) 273-284, 2008; Pascual-Figal, Hyperuricaemia and long-term outcome after hospital discharge in acute heart failure patients. Eur J Heart Fail. 2006 Oct. 23; [Epub ahead of print]; Cengel, A., et al., "Serum uric Acid Levels as a Predictor of In-hospital Death in Patients Hospitalized for Decompensated Heart Failure." Acta Cardiol. (October 2005) 60(5): 489-492), myocardial infarctions (Strasak, A. M. et al.; Bos et al., Uric acid is a risk factor for myocardial infarction and stroke: the Rotterdam study. Stroke. 2006 June; 37(6):1503-7), renal dysfunction (Cirillo et al., Uric Acid, the metabolic syndrome, and renal disease. J Am Soc Nephrol. 17(12 Suppl 3):S165-8, 2006), and strokes (Bos et al., 2006). Uric acid directly causes endothelial dysfunction (Kanellis, et al., Uric acid as a mediator of endothelial dysfunction, inflammation, and vascular disease. Semin Nephrol. 25(1):39-42, 2005; Khosla et al, Hyperuricemia induces endothelial dysfunction. Kidney Int. 67(5): 1739-42, 2005). In children, early-onset essential hypertension is associated with elevated serum uric acid, and reduction of uric acid with allopurinol reduced blood pressure in a small cohort of patients (Feig and Johnson, The role of uric acid in pediatric hypertension. J Ren Nutrition 17(1): 79-83, 2007). Hyperuricemia is an independent risk factor in all of these conditions.

Elevated soluble uric acid is also associated with or directly induces inflammatory responses. For example, uric acid is transported into vascular smooth muscle cells via organic acid transporters, especially the urate transporter URAT1, and then stimulates vascular smooth muscle cells to produce C-reactive protein, MCP-1 and other cytokines, thereby stimulating proliferation and other changes associated with atherosclerosis (Price et al., Human vascular smooth muscle cells express a urate transporter. J Am Soc Nephrol. 17(7): 1791-5, 2006; Kang et al., Uric acid causes vascular smooth muscle cell proliferation by entering cells via a functional urate transporter. Am J Nephrol. 2005 25(5):425-33 (2005); Yamamoto et al., Allopurinol reduces neointimal hyperplasia in the carotid artery ligation model in spontaneously hypertensive rats. Hypertens. Res. 29 (11) 915-921, 2006), stimulates human mononuclear cells to produce IL-1β, IL-6 and TNF-α, causes marked increases in TNF-α when infused into mice, activates endothelial cells and platelets, and increases platelet adhesiveness (Coutinho et al., "Associations of Serum Uric Acid with Markers of Inflammation, Metabolic Syndrome, and Subclinical Coronary Atherosclerosis", Amer. J. Hypertens. (2007) 20: 83-89; Levya, F., et al., "Uric Acid in Chronic Heart Failure: A Marker of Chronic Inflammation", Eur. Heart J. (1998) 19(12): 1814-1822). Uric acid has also been shown to inhibit bioavailability of endothelial nitric oxide and activate the renin-angiotensin system.

Hyperuricemia is also associated with cognitive impairment and other forms of central nervous system dysfunction. (Schretlen, D. J. et al., "Serum Uric Acid and Cognitive Function in Community-Dwelling Older Adults", Neuropsychology (January 2007) 21(1): 136-140; Watanabe, S., et al., "Cerebral Oxidative Stress and Mitochondrial Dysfunction in Oxonate-Induced Hyperuricemic Mice", J. Health Science (2006) 52: 730-737).

Elevated serum uric acid levels are also associated with increased risk of cancer and cancer mortality. (Strasak, A M et al. (2007) Serum uric acid and risk of cancer mortality in a large prospective male cohort. Cancer Causes Control 18 (9) 1021-1029; Strasak, A M et al. (2007) The role of serum uric acid as an antioxidant protecting against cancer: prospective study in more than 28,000 older Austrian women. Annals Oncol 18 (11) 1893-1897; Jee, S A et al. (2004) Serum uric acid and risk of death from cancer, cardiovascular disease or all causes in men Eur. J. Cardiovascular Prev. Rehab. 11 (3) 185-191)

Elevated levels of uric acid are associated with prediabetes, insulin resistance, the development of Type 2 diabetes, and an increased probability of a variety of undesirable conditions in people with diabetes, such as peripheral artery disease, strokes, and increased mortality risk, (Ioachimescu, A. G. et al. (2007) Serum uric acid, mortality and glucose control in patients with Type 2 diabetes mellitus: a PreCIS database study Diabet. Med. 24 (12) 1369-1374; Perry, I. J. et al (1995) Prospective study of risk factors for development of non-insulin dependent diabetes in middle aged British men BMJ 310 (6979) 560-564; Chien, K-L et al. (2008) Plasma uric acid and the risk of Type 2 diabetes in a Chinese community Clin. Chem. 54 (2) 310-316; Sautin, Y. Y. et al. (2007) Adverse effects of the classic antioxidant uric acid in adipocytes: NADPH oxidase-mediated oxidative/nitrosative stress Am. J. Physiol. Cell Physiol. 293: C584-0596; Tseng, C. H. (2004) Independent association of uric acid levels with peripheral artery disease in Taiwanese patients with Type 2 diabetes Diabet. Med. 21 (7) 724-729; Lehto, S. et al. (1998) Serum uric acid is a strong predictor of stroke in patients with non-insulin dependent diabetes mellitus Stroke 29: 635-639

Elevated levels of uric acid are a defining feature of Lesch-Nyhan Syndrome. People with sleep apnea or sleep-disordered breathing also have elevated of uric acid (Saito, H. et al., Tissue hypoxia in sleep apnea syndrome assessed by uric acid and adenosine. Chest 122: 1686-1694, 2002; Verhulst, S. L., et al., Sleep-disordered breathing and uric acid in overweight and obese children and adolescents. Chest 132: 76-80, 2007)

Elevated uric acid is associated with preeclampsia (Bainbridge, S. A. and Roberts, J. M., Uric acid as a pathogenic factor in preeclampsia. Placenta Dec. 17, 2007 epub ahead of print).

There is a significant medical need for new medications that can safely, conveniently and effectively treat and prevent disorders related to elevation of blood uric acid, whether such diseases are due to crystallization of uric acid or to effects of supranormal (whether by an individual or a population-based standard) levels of soluble uric acid.

SUMMARY OF THE INVENTION

This invention concerns certain therapeutic uses of a Compound of Formula I or a pharmaceutically acceptable salt thereof.

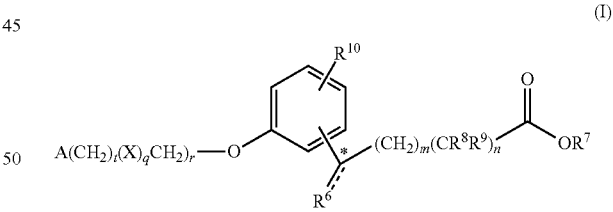

In Formula I, m is 0, 1, 2, 3 or 4; n is 0 or 1; t is 0 or 1; q is 0 or 1; and r is 0, 1 or 2. $R^6$ is hydrogen, O or hydroxyl. $R^7$ is hydrogen or alkyl having from 1 to 3 carbon atoms. One of $R^8$ and $R^9$ is alkyl having from 1 to 3 carbon atoms, and the other is hydrogen or alkyl having from 1 to 3 carbon atoms. $R^{10}$ is hydrogen, halo, alkyl having from 1 to 3 carbon atoms or alkoxy having from 1 to 3 carbon atoms. X is C(O) and r is 0 and t is 0; or X is $NH(R^{11})$ wherein $R^{11}$ hydrogen or alkyl having from 1 to 3 carbon atoms. A is phenyl, unsubstituted or substituted by 1 or 2 groups selected from halo, hydroxy, methyl, ethyl, perfluoromethyl, methoxy, ethoxy, and perfluoromethoxy; or a 5 or 6 membered heteroaromatic ring having 1 or 2 ring heteroatoms selected from N, S and O and the heteroaromatic ring is covalently bound to the remainder of the compound of Formula I by a ring carbon; or cycloalkyl having from 3 to 6 ring carbon atoms wherein the cycloalkyl is unsubstituted or one or two ring carbons are independently monosubstituted by methyl or ethyl. Esters and other prodrugs of compounds of Formula I are also included in this invention.

This invention provides a method of reducing the uric acid concentration in blood of, or increasing uric acid excretion from, a mammalian subject, comprising administering to the subject a Compound of Formula I or a pharmaceutically acceptable salt thereof in an amount effective to reduce the uric acid concentration in blood of, or increase uric acid excretion from, the subject. This invention provides the use of a biologically active agent in the manufacture of a medicament for reducing the uric acid concentration in blood of, or increasing uric acid excretion from, a mammal wherein the agent is a Compound of Formula I or a pharmaceutically acceptable salt thereof and is formulated for administration in an amount effective to reduce the uric acid concentration in blood of, or increase uric acid excretion from, the subject. This invention provides a pharmaceutical composition for use in reducing the uric acid concentration in blood of or increasing uric acid excretion from, a mammalian subject comprising a Compound of Formula I or a pharmaceutically acceptable salt thereof in an amount effective to reduce the uric acid concentration in blood of, or increase uric acid excretion from, the subject. This invention provides a kit comprising one or more unit oral doses of a Compound of Formula I or a pharmaceutically acceptable salt thereof, and instructions for administering the Compound of Formula I or pharmaceutically acceptable salt thereof to reduce the uric acid concentration in blood of, or increasing uric acid excretion from, a mammalian subject.

Reducing uric acid as described herein can be used to treat or prevent a variety of conditions including gout (any or all of: asymptomatic gout, acute gouty arthritis, intercritical gout, and chronic tophaceous gout), hyperuricemia, elevated levels of uric acid that do not meet the levels customarily justifying a diagnosis of hyperuricemia, renal dysfunction, kidney stones, cardiovascular disease, risk for developing cardiovascular disease and other consequences of hyperuricemia, cognitive impairment, and early-onset essential hypertension.

This invention is based on the observation that a compound of Formula I that was administered to humans reduced the level of uric acid in the blood of human patients and increased excretion of uric acid, as described in Examples 1 through 5. The in vivo experiments utilized a compound in which $R^6$ is O. Because Compounds CF and CR are metabolites of Compound BI, it is believed that Compounds of Formula I in which $R^6$ is hydrogen or hydroxy will also reduce in vivo blood levels of uric acid and increase excretion of uric acid. This invention is also based on the observation that compounds of Formula I, including compounds in which $R^6$ is O, hydrogen or hydroxy, inhibited URAT1 in vitro, as shown in Example 6. Inhibition of URAT1 is an established in vitro model for lowering uric acid in vivo.

This invention also provides the following compounds, their pharmaceutically acceptable salts, esters and prodrugs:
DQ 2-(3-(2,6-Dimethylbenzyloxy)-4-methoxyphenyl)acetic acid;
EB Methyl 3-(3-(2,6-dimethylbenzyloxy)phenyl)-3-oxopropanoate;
DR 2-(3-(2,6-Difluorobenzyloxy)phenyl)acetic acid;
DS 4-(3-(2,6-Dichlorobenzyloxy)phenyl)-4-oxobutanoic acid;
DT 2-(3-(2,6-Dimethylbenzyloxy)phenyl)propanoic acid;
DU 2-(3-(4-Trifluoromethyl)benzyloxy)phenyl)acetic acid;
DV 2-(3-(2,6-Dimethylbenzyloxy)phenyl)butanoic acid;
DW 2-(3-(3,5-Dimethylbenzyloxy)phenyl)acetic acid;
DX 2-(3-(2,4-Dimethylbenzyloxy)phenyl)acetic acid;
DY 2-(3-(2,6-Dimethoxylbenzyloxy)phenyl)butanoic acid;
DZ 2-(3-(Benzyloxy)phenyl)acetic acid; and
EA 2-(2-(2,6-Dimethylbenzyloxy)phenyl)acetic acid.

DETAILED DESCRIPTION OF THE INVENTION

Definitions

Figure 1:
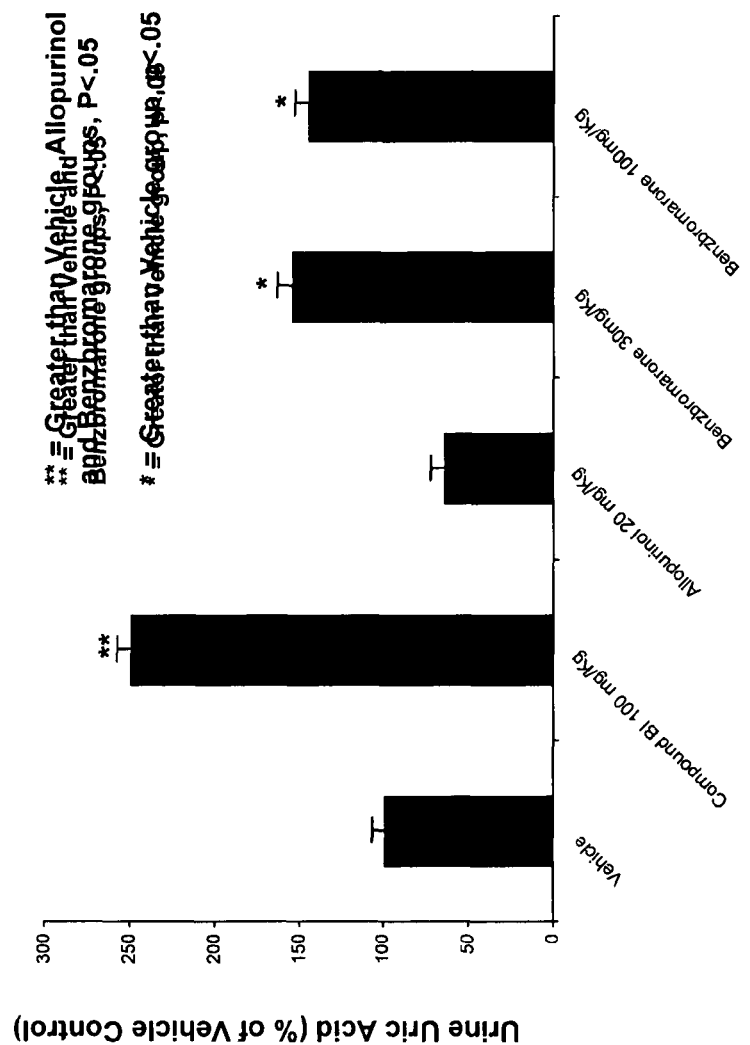
FIG. 1: Compound BI increases excretion of uric acid in urine of mice treated with the uricase inhibitor potassium oxonate.

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, and bromo.

As used herein the term "perfluoro" as in perfluoromethyl or perfluoromethoxy, means that the group in question has fluorine atoms in place of all of the hydrogen atoms.

The bond between $R^6$ and the carbon atom to which it is directly bonded is depicted in Formula I above by a solid line together with a dashed line. This depiction reflects that the bond in question can be either a single bond, when $R^6$ is hydrogen or hydroxy, or a double bond, when $R^6$ is O.

The asterisk in the depiction of Formula I above indicates a possible chiral center, and that carbon is chiral when $R^6$ is hydroxy. In such cases, this invention provides the racemate, the (R) enantiomer, and the (S) enantiomer, of the Compounds of Formula I, all of which are believed to be active. In the synthesis examples a racemate is indicated by a wavy bond. Mixtures of these enantiomers can be separated by using HPLC, for example as described in Chirality 11:420-425 (1999).

The term "prodrug(s)" of a compound of interest refers to other compounds that are cleaved, typically in vivo, to yield the compound of interest.

Certain chemical Compounds are referred to herein by their chemical name or by the two-letter code shown below. The compounds listed below are included within the scope of Formula I shown above.
BI 4-(3-(2,6-Dimethylbenzyloxy)phenyl)-4-oxobutyric acid
CF 3-(2,6-Dimethylbenzyloxy)phenylacetic acid
CR 4-(3-(2,6-Dimethylbenzyloxy)-phenyl)-4(R)-hydroxybutanoic acid
DQ 2-(3-(2,6-Dimethylbenzyloxy)-4-methoxyphenyl)acetic acid
AN 4-(3-(2-Methylbenzyloxy)phenyl)-4-oxobutanoic acid
AW 4-(3-(2,6-Difluorobenzyloxy)phenyl)-4-oxobutanoic acid
BJ 4-(3-(2-Fluoro-6-methylbenzyloxy)phenyl)-4-oxobutanoic acid BP 4-(3-(2,6-Dimethylbenzyloxy)phenyl)-2,2-dimethyl-4-oxobutanoic acid
BS 4-(3-(2,6-Dimethylbenzyloxy)phenyl)butanoic acid
EB Methyl 3-(3-(2,6-dimethylbenzyloxy)phenyl)-3-oxopropanoate
CD 5-(3-(2,6-Dimethylbenzyloxy)phenyl)-5-oxopentanoic acid
CQ 2-(3-(2,6-Dimethylbenzyloxy)phenyl)-2-oxoacetic acid
CK 5-(3-(2,6-Dimethylbenzyloxy)phenyl)pentanoic acid
CM 3-(3-(2,6-Dimethylbenzyloxy)phenyl)propanoic acid
DR 2-(3-(2,6-Difluorobenzyloxy)phenyl)acetic acid
DS 4-(3-(2,6-Dichlorobenzyloxy)phenyl)-4-oxobutanoic acid
DT 2-(3-(2,6-Dimethylbenzyloxy)phenyl)propanoic acid
DU 2-(3-(4-Trifluoromethyl)benzyloxy)phenyl)acetic acid
DN 2-(3-(2,4-bis(trifluoromethyl)benzyloxy)phenyl)acetic acid
DV 2-(3-(2,6-Dimethylbenzyloxy)phenyl)butanoic acid
DW 2-(3-(3,5-Dimethylbenzyloxy)phenyl)acetic acid
DX 2-(3-(2,4-Dimethylbenzyloxy)phenyl)acetic acid
DY 2-(3-(2,6-Dimethoxylbenzyloxy)phenyl)acetic acid
DZ 2-(3-(Benzyloxy)phenyl)acetic acid
BH 4-(3-(Cyclopropylmethoxy)phenyl)-4-oxobutanoic acid
DP 4-(3-(2,6-Dimethylbenzoyloxy)phenyl)-4-oxobutanoic acid
AB 4-(4-(2-Methoxybenzyloxy)phenyl)-4-oxobutanoic acid
AF 4-oxo-4-(4-(pyridin-2-ylmethoxy)phenyl)butanoic acid
AG 4-(4-(Benzyloxy)phenyl)-4-oxobutanoic acid
AH 4-(4-(2,6-Difluorobenzyloxy)phenyl)-4-oxobutanoic acid
AI 4-(4-(2-Chlorobenzyloxy)phenyl)-4-oxobutanoic acid
AM 4-(4-(2-((2-Fluorobenzyl)(methyl)amino)ethoxy)phenyl)-4-oxobutanoic acid hydrochloride
AT 4-(4-(2,5-Dimethylbenzyloxy)phenyl)-4-oxobutanoic acid
AY 4-(4-(2-Trifluoromethylbenzyloxy)phenyl)-4-oxobutanoic acid
BM 4-(4-(2,6-Dimethylbenzyloxy)phenyl)-4-oxobutanoic acid
BT 4-(4-(2,6-Dimethylbenzyloxy)-3-methoxyphenyl)-4-oxobutanoic acid
DO 2-(4-(2,6-Dimethylbenzyloxy)phenyl)acetic acid
EA 2-(2-(2,6-Dimethylbenzyloxy)phenyl)acetic acid As used herein the transitional term "comprising" is open-ended. A claim utilizing this term can contain elements in addition to those recited in such claim.

As used in the claims the word "or" means "and/or" unless such reading does not make sense in context. So for example the phrase "reducing the uric acid concentration in blood of or increasing uric acid excretion from, a mammalian subject" is equivalent to "reducing the uric acid concentration in blood of and/or increasing uric acid excretion from, a mammalian subject.

Compounds of the Invention

In an embodiment of the invention described in the Summary above, A is substituted (as defined above) or unsubstituted phenyl, for example 2,6-dimethylphenyl. In other embodiments r is 1, t is 0, and q is 0. In another embodiment $R^{10}$ is methoxy.

The two bulky substituents (i.e. other than $R^{10}$) around the central phenyl ring can be located in the ortho, meta or para position with respect to one another. Preferably they are in the meta position with respect to one another.

In an embodiment of Formula I, A is substituted (as defined above) or unsubstituted phenyl, t is 0, q is 0, r is 1, $R^{10}$ is hydrogen, n is 0, m is 0, 2 or 4. In a more specific embodiment A is 2,6-dimethylphenyl.

In an embodiment of this invention the Compound is represented by Formula IA. In a more specific embodiment the Compound is represented by Formula IA1. In Formulas IA and IA1 the variables are as defined above. In more specific embodiments A is 2,6-dimethylphenyl, i.e. $R^1$ is methyl and $R^5$ is methyl. Nonlimiting examples of compounds of Formula I include Compounds AF, AG, AH, AT, BM, BT, DO and EA. Nonlimiting examples of compounds of Formula IA include Compounds BH and DP. Nonlimiting examples of compounds of Formula IA1 include Compounds BI, CF, CR, DQ, AN, AW, BJ, BP, BS, EB, CD, CQ, CK, CM, DR, DS, DT, DU, DN, DV, DW, DX, DY and DZ.

In an embodiment of Formula IA1, $R^{10}$ is hydrogen, m is 0, 2 or 4; and n is 0. Preferably $R^1$ is methyl and $R^5$ is methyl.

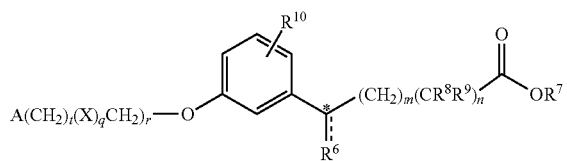

(IA)

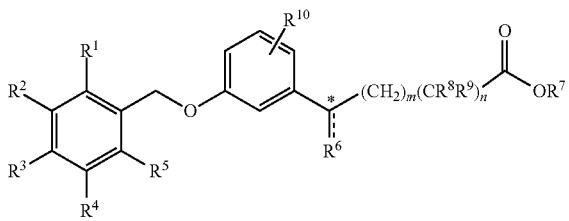

(IA1)

The compounds of Formula I can be made according to methods described in WO 02/100341, WO 04/073611, WO 04/091486, WO 04/098496, WO 07/087,506, WO 07/146,768, and U.S. Application No. 61/021,061, filed Jan. 15, 2008, the contents of which are incorporated herein by reference.

Use in Methods of Treatment

This invention provides a method for reducing uric acid levels in a mammalian subject or increasing uric acid excretion from a mammalian subject. The level of uric acid in a mammal can be determined using any conventional measure. Typically the level of uric acid in the blood is determined. Uric acid can also be deposited or precipitated in tissues, resulting in depots (e.g. tophi) that can be affected by raising or lowering blood uric acid concentrations, and which conversely can contribute to circulating uric acid. The method of this invention for reducing uric acid can be used to treat or prevent a variety of conditions including gout, hyperuricemia, elevated levels of uric acid that do not meet the levels customarily justifying a diagnosis of hyperuricemia, kidney stones, renal dysfunction, cardiovascular disease, cardiovascular risk factor, and cognitive impairment. By lowering uric acid levels, administration of the compounds of Formula I slows progression of kidney disease. An elevated uric acid level has been identified as a risk factor for cardiovascular disease. A significant correlation has been shown between elevated uric acid and cognitive impairment in older adults. (Schretlen, D. J. et al., "Serum Uric Acid and Cognitive Function in Community-Dwelling Older Adults", Neuropsychology (January 2007) 21(1): 136-140). Accordingly, the method of this invention for reducing uric acid can be used to treat or prevent cognitive impairment, including cognitive impairment in elderly adults. It is well known that people with Lesch-Nyhan Syndrome have elevated levels of uric acid and suffer the numerous consequences of this hyperuricemia, including gout. Thus, this invention for reducing blood levels and increasing elimination of uric acid can be used to treat people with Lesch-Nyhan Syndrome.

The normal range of uric acid in blood is between 3.4 mg/dL and 7.0 mg/dL in men, between 2.4 mg/dL and 6.0 mg/dL in premenopausal women, and from 2.5 mg/dL to 5.5 mg/dL in children. Urate crystal formation/precipitation typically occurs in men at levels of 6.6 mg/dL or higher and in women at levels of 6.0 mg/dL or higher. This illustrates that levels of uric acid that are within the so-called normal range can have undesirable health consequences, even producing gout. Also, what may be in the normal range for the population as a whole may be elevated for the individual. Cardiovascular and other consequences of elevated uric acid can occur with blood levels well within these "normal" ranges. Therefore, a diagnosis of hyperuricemia is not necessarily a prerequisite for the beneficial effects of the compounds of the invention.

This invention includes the treatment of hyperuricemia associated with gout, hypertension, vascular inflammation, heart failure, arterio-venous disorders, myocardial infarct, stroke, pre-eclampsia, eclampsia, sleep apnea, renal dysfunction (including renal failure, end stage renal disease [ESRD]), organ transplant, diuretics, thiazides, cyclosporine, aspirin, vitamin C, nicotinic acid, levodopa (L-DOPA), cytotosic drugs, and certain antibacterial agents (such as pyrozinamide), cirrhosis, thyroid dysfunction, parathyroid dysfunction, lung cancer, anemia, leukemia, lymphoma, multiple myeloma, tumor-lysis syndrome, thyroid or parathyroid dysfunction, Lesch-Nyhan Syndrome, smoking, alcohol consumption, and psoriasis. This invention includes the treatment of hyperuricemia that can lead to gout, formation of urate crystals, renal dysfunction, graft or organ failure following transplant, endothelial disorders (such as inflammation), chronic heart failure, arterio-venous disorders, pre-eclampsia, eclampsia, hypertension, and cognitive impairment. In embodiments of the method of this invention for treating gout, tissue deposits of uric acid, including but not limited to tophi, are reduced, and the incidence and severity of gout flares are also reduced.

The Compound of Formula I or salt thereof can be administered by any conventional route of systemic administration. Preferably they are administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitioneal injection), or nasally.

Further embodiments of each of the uses and methods of treatment of this invention comprise administering any of the embodiments of the Compound of Formula I or pharmaceutically salts thereof. In the interest of avoiding unnecessary redundancy, each such agent and group of agents is not being repeated, but they are incorporated into this description of uses and methods of treatment as if they were repeated.

Both human and non-human mammalian subjects can be treated in accordance with the treatment method of this invention. The optimal dose of a particular active agent of the invention for a particular subject can be determined in the clinical setting by a skilled clinician. In the case of oral administration the Compound of Formula I or pharmaceutically acceptable salt thereof is generally administered to adults in a daily dose of from 1 mg to 2500 mg, more preferably from 1 mg to 1200 mg, more preferably from 400 mg to 1000 mg, more preferably from 600 mg to 800 mg, more preferably from 600 mg to 1000 mg, administered once or twice per day. The average body weight of a typical adult is 60 to 70 kilograms, so that appropriate dose ranges expressed as mg/kg are approximately from 0.015 to 42 mg/kg, more preferably from 0.015 to 20 mg/kg, more preferably from 6.6 to 13 mg/kg, more preferably from 10 to 13 mg/kg mg, more preferably from 10 to 16 mg/kg, administered once or twice per day. When treating children the optimal dose is determined by the patient's physician. In the case of oral administration to a mouse the Compound of Formula I or pharmaceutically acceptable salt thereof is generally administered in a daily dose from 1 to 300 mg of the agent per kilogram of body weight.

The Compound of Formula I or pharmaceutically acceptable salt thereof can be administered in combination with other uric acid lowering drugs. In such cases the dose of the Compound of Formula I or its salts is as described above. Any conventional or investigational uric acid lowering drug can be utilized in combination with the compounds of Formula I. Examples of such drugs include xanthine oxidase inhibitors such as allopurinol (from 100 mg/day to 1000 mg/day; more typically from 100 mg/day to 300 mg/day) febuxostat (from 40 mg/day to 120 mg/day; more specifically from 60 mg/day to 80 mg/day) and oxypurinol; Puricase/PEG-uricase (from 4 mg to 12 mg every two weeks by infusion); uricosuric agents such as sulfinpyrazone (from 100 mg/day to 800 mg/day), probenecid (500 mg/day), losartan (from 25 mg/day to 200 mg/day, more typically from 50 mg/day to 100 mg/day), fenofibrate, JTT-552 (a URAT-1 inhibitor), benzbromarone (from 70 mg/day to 150 mg/day), and statins such as atorvastatin (LIPITOR®). The other uric acid lowering drug can be administered in its usual amount or in an amount that is less than the usual amount, whether by administering lower doses of such other drug or by less frequent dosing with such other drug.

The compounds of Formula I and their pharmaceutically acceptable salts can be administered together with other drugs used to decrease the pain associated with gouty attacks, for example nonsteroidal antiinflammatory drugs (NSAIDs), colchicine, corticosteroids, and other analgesics.

In the course of lowering uric acid levels in the blood it is expected that the compounds of Formula I will increase the levels of uric acid in the urine. To increase the pH of the urine and thereby improve solubility of the uric acid, citrate or bicarbonate, for example, can be administered in conjunction with the compound of Formula I.

An admixture of the compound or salt of Formula I with one or more other uric acid lowering drugs, analgesics, and pH increasing agents, can be administered to the subject. Alternatively the compound or salt of Formula I and the one or more other uric acid lowering drugs, analgesics, and pH increasing agents are not mixed together to form an admixture but are administered independently to the subject. When the active ingredients are not mixed together to form a single admixture or composition it is convenient to provide them in the form of a kit comprising one or more unit oral doses of a Compound of Formula I or a pharmaceutically acceptable salt thereof, one or more unit oral doses of one or more other uric acid lowering drugs, analgesics, and pH increasing agents, and instructions for administering the Compound of Formula I or pharmaceutically acceptable salt thereof in combination with the other active ingredients. Preferably the components of the kit are packaged together, such as in a box or a blister pack.

Pharmaceutical Compositions

This invention provides a pharmaceutical composition comprising a compound of Formula I or a pharmaceutically acceptable salt thereof, and optionally a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 2500 mg, more preferably from 1 mg to 1200 mg, preferably from 400 mg to 1000 mg, more preferably from 600 mg to 800 mg, more preferably from 600 mg to 1000 mg, of the compound of Formula I or its salt. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The active ingredients can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants.

The invention will be better understood by reference to the following examples, which illustrate but do not limit the invention described herein.

EXAMPLES

Example 1

Five groups of 4 healthy, normal men and women received a single, oral administration of escalating doses of Compound BI (n=3 per group) or placebo capsules (n=1 per group) in a randomized, double blind clinical study. Blood uric acid levels were measured before and 24 hours after administration of study treatment. Compound BI was administered at doses of 50, 100, 200, 400 or 800 mg.

Administration of a single dose of Compound BI resulted in a significant, dose-dependent reduction in uric acid levels. Uric acid levels were elevated in subjects receiving placebo. (Table 1)

TABLE 1

Percent Change in Uric Acid Levels Following a Single Administration of Study Treatment

| Study Treatment | | (N) | Mean Percent Change |
|---|---|---|---|
| Placebo | | (5) | +8.4 |
| BI | 50 | (3) | −8.8 |
| BI | 100 | (3) | −13.4 |
| BI | 200 | (3) | −18.9 |
| B1 | 400 | (3) | −35.0 |
| BI | 800 | (3) | −32.7 |

Example 2

Two groups of 8 healthy normal men and women received oral administration of either 800 mg Compound BI once per day (n=6 per group) or 400 mg Compound BI twice per day (n=6 per group) or placebo capsules (n=2 per group) in a randomized, double blind clinical study. Blood uric acid levels were measured before administration of study treatment, 24 hours after the first administration of study treatment and after 7 consecutive days of study treatment administration.

Administration of a single dose of Compound BI resulted in a significant reduction in uric acid levels in both groups of patients receiving Compound BI (Table 2), as did daily administration for 7 days (Table 3). Uric acid levels in patients receiving placebo capsules were elevated compared to baseline 24 hours after the first administration and unchanged after receiving placebo daily for 7 days.

TABLE 2

Percent Change in Uric Acid Levels Following a Single Administration of Study Treatment for Seven Days Treatment

| Study Treatment | (N) | Mean Percent Change |
|---|---|---|
| Placebo | (4) | +4.9 |
| BI 400 bid. | (6) | −54.0 |
| BI 800 qd | (6) | −45.3 |

TABLE 3

Percent Change in Uric Acid Levels Following a Daily Administration of Study Treatment for Seven Days

| Study Treatment | (N) | Mean Percent Change |
|---|---|---|
| Placebo | (4) | +0.5 |
| BI 400 bid. | (6) | −56.7 |
| BI 800 cid | (6) | −53.2 |

Example 3

Compound BI Increases Uric Acid Excretion in Urine of Mice Treated with the Uricase Inhibitor Potassium Oxonate The model to induce hyperuricemia involves the use of the uricase (urate oxidase) inhibitor potassium oxonate that causes a delay in the degradation of uric acid to allantoin. Humans have little or no uricase activity, so inhibition of this enzyme with potassium oxonate makes mouse uric acid processing more similar to that of humans.

Male 11-week old C57/Bl6 mice (Harlan, Frederick, Md.) were used in the studies (8 per experimental group). Mice were receiving standard rodent chow that was removed one hour before administration of potassium oxonate. Mice were given an intraperitoneal injection (i.p.) of potassium oxonate (300 mg/kg) that was suspended in 0.5% hydroxypropylmethylcellulose (HPMC). After 90 minutes, mice received treatments by oral administration of allopurinol (20 mg/kg; Sigma, Saint Louis, Mo.), benzbromarone (30 or 100 mg/kg; Sigma) or Compound BI (100 mg/kg) or vehicle (1% HPMC) and urine collection was started. Urine collection was performed at 1, 3 and 5 hours after drug treatments and uric acid was measured with a colorimetric assay (BioVision Research Products, Mountain View, Calif.).

In urine collected between 3 and 5 hours after drug administration, Compound BI induced a significant increase in excreted uric acid versus the Oxonate control group. Benzbromarone at both doses also induced an increase in uric acid concentration in urine, though to lesser degree than Compound BI. Allopurinol, which inhibits uric acid synthesis in the liver and other tissues, reduced the concentration of uric acid in urine. (Table 4 and FIG. 1).

TABLE 4

| Experimental Group | Urine Uric Acid (mg/dL) |
|---|---|
| Oxonate 300 mg/kg i.p. (Control) | 118 ± 7 |
| Oxonate i.p + Cpd BI 100 mg/kg p.o. | 293 ± 13 ** |
| Oxonate i.p. + Allopurinol 20 mg/kg p.o. | 79 ± 5 |
| Oxonate i.p + Benzbromarone 30 mg/kg p.o. | 185 ± 12 * |
| Oxonate i.p + Benzbromarone 100 mg/kg p.o. | 173 ± 8 * |

* Greater than Oxonate group, P < .05
** Greater than Oxonate, Benzbromarone or Allopurinol groups, P < .05

Example 4

Plasma samples taken immediately prior to and at 1, 2, 4, 6, 12 and 24 hours after a single, oral administration of a test compound to 4 healthy, normal men and women in each of three groups as described above in Example 1 were analyzed to determine uric acid levels. Compound BI (n=3 per group) or placebo capsules (n=1 per group) were administered in a randomized, double blind clinical study. Plasma samples taken at the time points indicated from patients receiving Compound BI at doses of 200, 400 or 800 mg were stored at −70° C. and analyzed at a later time.

Figure 2:
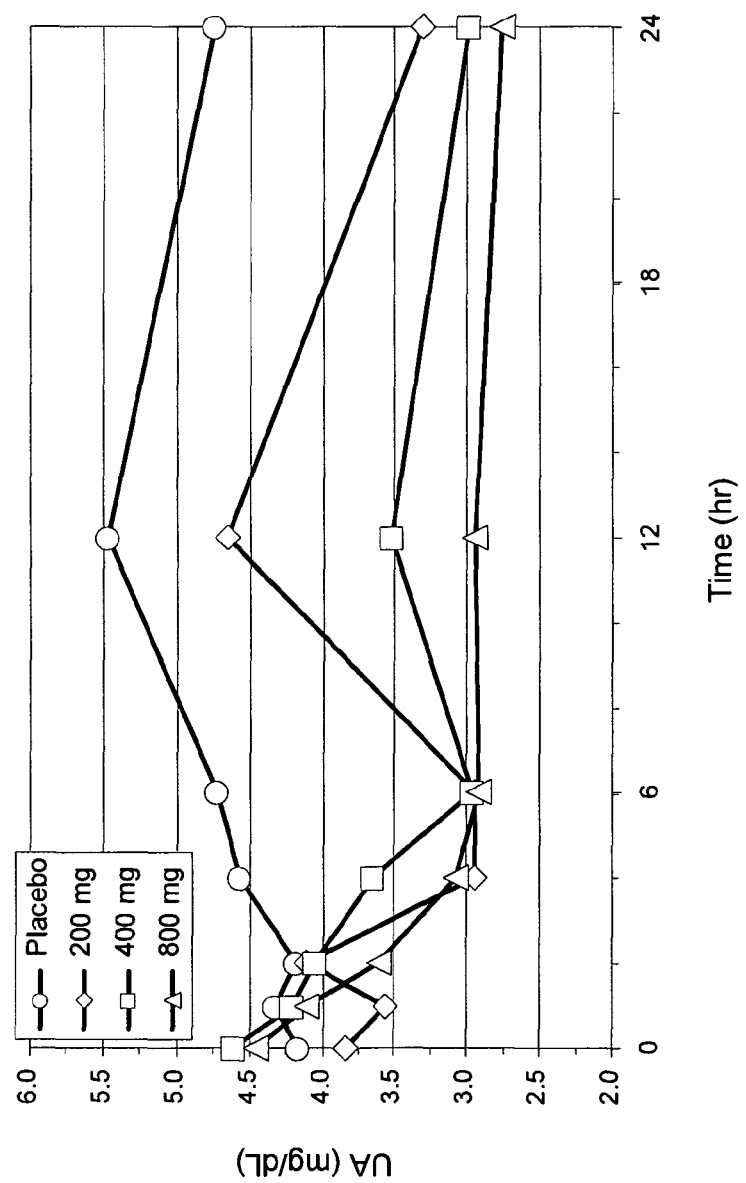
FIG. 2: Plasma UA (uric acid) levels over the initial 24-hour period in patients receiving various doses of Compound BI.

Administration of a single dose of Compound BI resulted in significant, dose-dependent reductions in uric acid levels in all three groups (FIG. 2). Uric acid levels were elevated compared to baseline values throughout the 24-hour period in subjects receiving placebo. Uric acid levels in the subjects receiving placebo steadily increased from baseline through 12 hours and then declined to near-baseline levels at 24 hours, reflecting a daily rhythm in serum uric acid levels. In contrast, uric acid levels in all subjects receiving Compound BI declined to or near to the lowest levels for each group through the 6-hour time point. Uric acid levels of the group receiving the highest dose of Compound BI were nearly identical at the 6 and 12-hour time points, and declined further between 12 and 24 hours.

These results indicate that administration of Compound BI can reduce the levels of uric acid throughout a 24-hour period compared to placebo administration and that administration of the highest single dose of Compound BI, 800 mg, resulted in the lowest levels of uric acid throughout the 24-hour period.

Example 5

Sixteen men and women participating in a clinical study were randomly assigned to receive either placebo capsules (n=4 subjects), 400 mg Compound BI twice per day (n=6 subjects), or 800 mg Compound BI once per day (n=6 subjects) for seven consecutive days. Plasma samples taken prior to (Time 0) and at 1, 2, 4, 9, 11, 13, 18 and 24 hours after the initial administration of the test article on Day 7 of the study were stored at −70° C. and later analyzed for uric acid. (This Example 5 is a continuation of the experiment described in Example 2.)

Uric acid levels in both groups of subjects receiving Compound BI were significantly reduced at Time 0 on Day 7 compared to Time 0 on the first day of the study and compared to placebo values throughout either day. Uric acid levels in the groups treated with Compound BI remained significantly below placebo values throughout Day 7 (FIG. 3).

Figure 3:
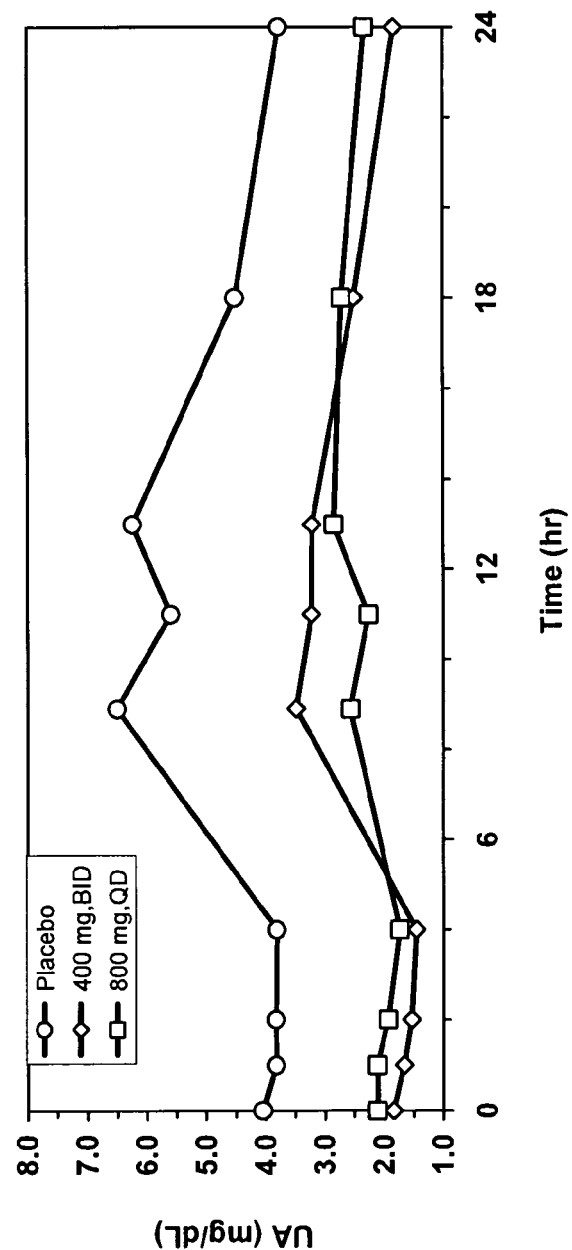
FIG. 3: Plasma UA (uric acid) levels over a 24-hour period on Day 7 of patients receiving various doses of Compound BI.

Uric acid levels throughout Day 7 in the subjects receiving placebo capsules daily over the 7-day course of the study were virtually unaffected by the placebo and were quite comparable to placebo values observed during the first 24-hour period of the study described in Example 4 as can be seen by comparing FIG. 3 with FIG. 2. (Example 4/FIG. 2 involved a different group of patients from Example 5/FIG. 3.)

These results show that daily administration of Compound BI for seven days reduced patient exposure to uric acid to an even greater extent than observed with a single day of treatment.

Example 6

URAT1 Inhibition Assay

URAT1 (Uric Acid Transporter 1) is expressed on the apical membrane in renal tubules. It mediates the re-uptake of uric acid from the urine into the blood. Inhibition of URAT1 leads to increased excretion of uric acid in the urine, and is therefore a potential mode of action for drugs that lower serum uric acid concentrations. Probenecid and Benzbromarone, for example, have been used clinically for treatment of gout and hyperuricemia, and they both act on URAT1 to reduce uric acid reuptake. However, benzbromarone was withdrawn from the market due to liver toxicity via mechanisms independent of URAT1, and probenecid acts on numerous transporter proteins, resulting in interactions with a variety of other drugs.

An in vitro URAT1 assay is useful for identifying compounds with potential activity in lowering serum uric acid. A suitable assay involves transfection of cells (e.g. human embryonic kidney cells; "HEK") with a vector encoding human URAT1, followed by determination of the ability of transfected cells to take up radiolabeled uric acid. The activity of compounds as URAT1 inhibitors is evaluated by their ability to block uric acid uptake by transfected cells.
Test Compounds and Chemicals:
Benzbromarone (Sigma, Cat. No. B5774), Probenecid (Sigma, Cat. No. P8761)), DMSO (Sigma, Cat. No. D-2650), [8-$^{14}$C] Urate (50-60 mCi/mmol; American Radio Chemicals, Cat. No. ARC0513).

Subcloning of hURAT1 into the expression vector:
Plasmid vector pCMV6-XL5 containing hURAT1 cDNA (Cat. No. SC125624) and the expression vector pCMV6-Neo (Cat. No. pCMVNEO) were obtained from OriGene Technologies, Inc. The full-length hURAT1 cDNA was obtained from the vector pCMV6-XL5 and subcloned into the expression vector pCMV6-Neo to create the hURAT1 expression plasmid pCMV6-hURAT1. The sequences were verified by automatic DNA sequencing.

Cell Culture, transfection of URAT1 expressing plasmids and the establishment of stably expressing HEK cells for hURAT1:

Human embryonic kidney 293 (HEK) cells (ATTCC, Cat No. CRL-1573) were cultured in EMEM supplemented with 10% FBS and 2 mM L-glutamine and incubated at 37° C. and 5% $CO_2$. For transfection experiments, cells were plated on 60 mm dishes in 1 ml media per dish. After an 18-24 hour incubation, cells were transfected with plasmid pCMV6-hURAT1 or the expression vector pCMV6-Neo, using the Lipofectin transfection agent following the manufacturer's instructions (Invitrogen, Cat. No. 18292). After transfection cells were grown in EMEM media for 72 hours and then by adding 1 mg/ml Geneticin (GIBCO, Cat. No 10131) stable transfectants were selected. Stable transfectants expressing hURAT1 (herein after referred as hURAT1-HEK cells) or cells having only the expression vector pCMV6-Neo (herein after referred as mock-HEK cells) were verified using reverse transcription polymerase chain reaction (RT-PCR) methods.

[8-$^{14}$C] Urate Uptake Assay:

hURAT1-HEK cells and mock-HEK cells were plated in poly-D-Lysine Cell culture 24 well plates (Becton Dickinson, Cat. No. 354414) at a concentration of $3\times10^5$ in EMEM medium and incubated overnight. Reaction solutions containing the [8-$^{14}$C] urate (55 mCi/mmol) at a final concentration of 50 µM were prepared with or without test compounds in Hanks' balanced salt solution (HBSS) containing 125 mM sodium gluconate, 4.8 mM potassium gluconate, 1.3 mM calcium, 5.6 mM glucose, 1.2 mM magnesium sulfate, 1.2 mM $KH_2PO_4$ and 25 mM HEPES (pH7.4). Before the uptake assay started, the culture medium was removed and the cells were incubated for 5 min in 0.6 ml of HBSS. After that HBSS was removed, the prepared reaction solutions were added into each well and incubated for 5 min at room temperature. Then the reaction solution was removed, cells were washed twice with 0.6 ml of cold HBSS and lysed with 0.2 ml of 0.1 M NaOH for 20 min. The cell lysates were transferred into the scintillation vials containing 1 ml of scintillation fluid (Opti Phase Super-MIX, PerkinElmer, Cat No. 1200-439) and the radioactivity was counted in the Microbeta counter (1450, Wallac Jet, PerkinElmer). Test compounds were dissolved in DMSO and the same concentration of DMSO was added into the wells of mock-HEK cells and the hURAT1-HEK cells that didn't contain test compounds. For each test compound, the uptake assay was performed 2 times and carried out in triplicate. Urate uptake of the cells for each test condition was presented as the average percent inhibition in comparison to the DMSO control. The radioactivity values obtained for the wells that contained DMSO were taken as 100% uptake of the cells. The observed concentration—percent inhibition data were fitted to a sigmoidal concentration-effect model, where:

$$IC50\hat{\ }Slope=[(100*Conc\hat{\ }Slope)/\% \text{ Inhibition}]-Conc\hat{\ }Slope$$

$IC_{50}$ and slope estimates with their 95% confidence limits were determined by a non-linear, least-squares regression analysis using the Data Analysis Toolbox™ (MDL Information Systems, San Leandro, Calif., USA).

For assessment of activity of compounds as URAT1 inhibitors, the percent inhibition of uric acid uptake was typically assessed at a drug concentration of 10 micromolar (Table 5). Additional drug concentrations were tested for determination of IC-50 values for some compounds (Table 6).

TABLE 5

Inhibitory effects of the test compounds at a concentration of at 10 µm on $^{14}$Curate uptake in hURAT1-HEK cells

| Test Compound | % of Inhibition | S.D. |
|---|---|---|
| AB | 3.7 | 3.29 |
| AF | 41.30 | 7.97 |
| AG | 5.99 | 4.39 |
| AH | 26.78 | 2.97 |
| AI | 2.3 | 0.25 |
| AM | 0.0 | 0.0 |
| AN | 54.44 | 3.47 |
| AT | 7.95 | 2.60 |
| AW | 61.93 | 1.61 |
| AY | 8.9 | 2.14 |
| BH | 62.40 | 5.47 |
| BI | 86.07 | 0.46 |
| BJ | 81.76 | 1.41 |
| BM | 22.21 | 2.20 |
| BP | 76.50 | 4.63 |
| BS | 28.60 | 6.38 |
| BT | 51.80 | 2.55 |
| CF | 96.50 | 1.13 |
| EB | 21.57 | 0.48 |
| CD | 63.5 | 0.44 |
| CQ | 84.84 | 0.36 |
| DP | 60.51 | 1.24 |
| CK | 88.00 | 0.84 |
| CM | 88.96 | 1.18 |
| CR | 60.60 | 3.70 |
| DR | 68.30 | 0.47 |
| DS | 75.00 | 1.00 |
| DT | 89.12 | 0.48 |
| DU | 30.52 | 2.10 |
| DN | 45.38 | 0.79 |
| DV | 79.55 | 0.79 |
| DO | 80.30 | 0.29 |
| DQ | 99.40 | 1.01 |
| EA | 49.00 | 1.36 |
| DW | 54.00 | 4.34 |
| DX | 64.00 | 1.79 |
| DY | 85.20 | 1.73 |
| DZ | 26.90 | 6.22 |

TABLE 6

| Compound | IC50 values (µM) |
|---|---|
| CQ | 1.33 |
| CM | 1.01 |
| CK | 2.69 |
| DT | 0.33 |
| DQ | 0.18 |
| DY | 1.88 |
| CF | 0.53 |
| BI | 0.95 |
| DV | 0.89 |
| BP | 4.39 |
| Benzbromarone | 0.75 |
| Probenecid | 174 |

Example 7

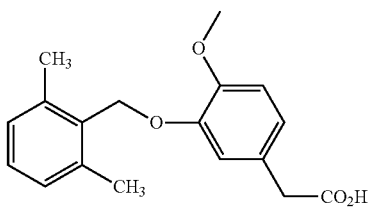 [SMILES: COc1ccc(CC(=O)O)cc1OCc1c(C)cccc1C]

2-(3-(2,6-Dimethylbenzyloxy)-4-methoxyphenyl)
acetic acid

Step A: Preparation of Ethyl 2-(3-hydroxy-4-methoxyphenyl)acetate

The stirred solution of 2-(3-Hydroxy-4-methoxyphenyl)acetic acid (9.82 g, 53.90 mmol) and p-Toluenesulfonic acid monohydrate (1.15 g, 6.0 mmol) in abs ethanol (100 ml) was refluxed for 4 hours or until all the starting material is consumed. The reaction mixture was concentrated, diluted with ethyl acetate and washed with 1M HCl. The organic layer was dried over $Na_2SO_4$, filtered, concentrated, and purified by flash chromatography on a silica gel column (hex:ethyl acetate 2:1) to give the title compound.

$^1$H NMR (270 MHz, CDCl$_3$): 1.2 (t, 3H); 3.6 (s, 2H); 3.8 (s, 3H); 4.1 (q, 2H); 6.6-6.8 (m, 3H).

Step B: Preparation of Ethyl 2-(3-(2,6-dimethylbenzyloxy)-4-methoxyphenyl)acetate A solution of 2,6-Dimethylbenzyl alcohol (3.23 g, 23.7 mmol) and diisopropyl azodicarboxylate (DIAD, 5.23 g, 25.9 mmol) in THF (20 ml) was added drop wise to a solution of Ethyl 2-(3-Hydroxy-4-methoxyphenyl)acetate (Step A, 5.48 g, 26.12 mmol) and triphenylphosphine (6.79 g, 25.9 mmol) in THF (100 ml) at 0° C. The reaction mixture was stirred at room temperature for 4 hours, diluted with ether and washed with water and brine. The organic layer was dried over $Na_2SO_4$, filtered, concentrated, and purified by flash chromatography on a silica gel column (hex:ethyl acetate 4:1) to give the title compound.

$^1$H NMR (270 MHz, CDCl$_3$): 1.2 (t, 3H); 2.3 (s, 6H); 3.5 (s, 2H); 3.8 (s, 3H); 4.1 (q, 2H); 5.1 (s, 2H); 6.9 (m, 2H); 7.15-7.35 (m, 4H).

Step C: Preparation of 2-(3-(2,6-Dimethylbenzyloxy)-4-methoxyphenyl)acetic acid To a stirred solution of Ethyl 2-(3-(2,6-dimethylbenzyloxy)-4-methoxyphenyl)acetate (Step B, 7.86 g, 24 mmol) in absolute ethanol (120 ml) was added 1N NaOH (50 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over $Na_2SO_4$, filtered, concentrated and purified by flash chromatography on a silica gel column (chloroform:methanol 95:5 spiked with acetic acid) to give the title compound as a white solid.

$^1$H NMR (270 MHz, CDCl$_3$): 2.3 (s, 6H); 3.5 (s, 2H); 3.8 (s, 3H); 5.1 (s, 2H); 6.9 (m, 2H); 7.15-7.35 (m, 4H).

Example 8

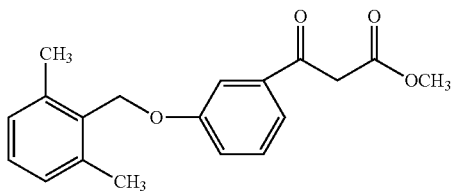 [SMILES: COC(=O)CC(=O)c1cccc(OCc2c(C)cccc2C)c1]

Methyl 3-(3-(2,6-dimethylbenzyloxy)phenyl)-3-oxo-propanoate

Step A: Preparation of Methyl 3-(3-(2,6-dimethylbenzyloxy)phenyl)-3-oxopropanoate To a solution of 3-(2,6-Dimethylbenzyloxy)acetophenone (10.40 g, 43.3 mmol) and dimethyl carbonate (64 ml) in DMF (100 ml) was added NaH (60% oil dispersion, 2.38 g, 99 mmol). The resulting mixture was stirred at room temperature for 2 hours, quenched with aqueous HCl and extracted with diethyl ether (2×). The combined organic layers were washed with water, brine, dried over $Na_2SO_4$, filtered, concentrated and purified by flash chromatography eluted with hexane:ethyl acetate (2:1) to give the title compound.

$^1$H NMR (270 MHz, CDCl$_3$): 2.4 (s, 6H); 3.8 (s, 3H); 4.0 (s, 2H); 5.1 (s, 2H); 7.1 (dd, 2H); 7.2 (m, 2H); 7.4 (t, 1H); 7.5-7.6 (m, 2H).

Example 9

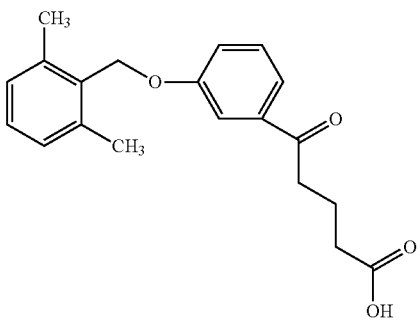 [SMILES: Cc1cccc(C)c1COc1cccc(C(=O)CCCC(=O)O)c1]

5-(3-(2,6-Dimethylbenzyloxy)phenyl)-5-oxopentanoic acid

Step A: Preparation of Ethyl 3-(3-(2,6-dimethylbenzyloxy)phenyl)-3-oxopropanoate To a solution of 3-(2,6-Dimethylbenzyloxy)acetophenone (5.20 g, 21.6 mmol) and diethyl carbonate (43.49 g, 368 mmol) in DMF (50 ml) was added NaH (60% oil dispersion, 1.61 g, 40.2 mmol). The resulting mixture was stirred at room temperature for 2 hours, quenched with aqueous HCl and extracted with diethyl ether (2×). The combined organic layers were washed with water, brine, dried over $Na_2SO_4$, filtered, concentrated and purified by flash chromatography eluted with hexane:ethyl acetate (4:1) to give the title compound.

$^1$H NMR (270 MHz, CDCl$_3$): 1.3 (t, 3H); 2.4 (s, 6H); 4.0 (s, 2H); 4.1 (q, 2H); 5.1 (s, 2H); 7.1 (dd, 2H); 7.2 (m, 2H); 7.4 (t, 1H); 7.5-7.6 (m, 2H).

Step B: Preparation of Diethyl 2-(3-(2,6-dimethylbenzyloxy)benzoyl)pentanedioate To a solution of Ethyl 3-(3-(2,6-dimethylbenzyloxy)phenyl)-3-oxopropanoate (Step A, 5 g, 16.02 mmol) in t-butyl alcohol (50 ml) was added a solution of potassium tert-butoxide (1M in t-butyl alcohol, 1.988 g, 17.7 mmol) and the reaction mixture was stirred for 30 minutes at room temperature. Ethyl 3-bromopropionate was added drop wise to the reaction mixture and stirring continued for another 2 hours and then poured into 1M HCl, extracted with ethyl acetate (2×), washed with brine, dried over Na$_2$SO$_4$, filtered, concentrated and purified by flash chromatography eluted with hexane:ethyl acetate (2:1) to give the title compound.

Step C: Preparation of 5-(3-(2,6-Dimethylbenzyloxy)phenyl)-5-oxopentanoic acid

To a solution of Diethyl 2-(3-(2,6-dimethylbenzyloxy)benzoyl)pentanedioate (Step B, 1.66 g, 4.0 mmol) in methanol (50 ml) was added 1N NaOH (17 ml) at the room temperature. The reaction mixture was stirred for 14 hours or until all the starting material is gone, concentrated, diluted in chloroform, and washed with 1M HCl to bring the pH to 3.5 to 4. The organic layer was washed with brine, dried over Na$_2$SO$_4$, filtered, concentrated and purified by flash chromatography eluted with chloroform:methanol (95:5 spiked with acetic acid) to give the title compound.

$^1$H NMR (270 MHz, CDCl$_3$): 2.1 (m, 2H); 2.4 (s, 6H); 2.5 (t, 2H); 3.1 (t, 2H); 5.1 (s, 2H); 7.1 (dd, 2H); 7.2 (m, 2H); 7.4 (t, 1H); 7.5-7.6 (m, 2H).

Example 10

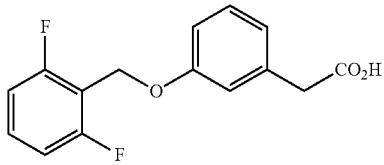 [SMILES: O=C(O)Cc1cccc(OCc2c(F)cccc2F)c1]

2-(3-(2,6-Difluorobenzyloxy)phenyl)acetic acid

Step A: Preparation of Ethyl 2-(3-hydroxyphenyl)acetate

The stirred solution of 2-(3-Hydroxyphenyl)acetic acid (25 g, 164.3 mmol) and p-Toluenesulfonic acid monohydrate (3.49 g, 18.3 mmol) in abs ethanol (250 ml) was refluxed for 4 hours or until all the starting material is consumed. The reaction mixture was concentrated, diluted with ethyl acetate and washed with 1M HCl. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 1.2 (t, 3H); 3.6 (s, 2H); 4.1 (q, 2H); 6.6-6.8 (m, 3H).

Step B: Preparation of Ethyl 2-(3-(2,6-difluorobenzyloxy)phenyl)acetate

To a stirred solution of Ethyl 2-(3-hydroxyphenyl)acetate (4 g, 22.2 mmol) in DMF (20 ml) was added potassium carbonate (4 g, 28.9 mmol) at room temperature followed by drop wise addition of 2,6-Difluorobenzyl bromide (5.06 g, 24.4 mmol). The reaction mixture was stirred for 12 hours and taken in ethyl acetate, washed with water (2×), brine, dried over Na$_2$SO$_4$, filtered, concentrated and purified by flash chromatography on a silica gel column (hex:ethyl acetate 4:1) to give the title compound.

$^1$H NMR (270 MHz, CDCl$_3$): 1.2 (t, 3H); 3.6 (s, 2H); 4.1 (q, 2H); 5.1 (s, 2H); 6.9 (m, 5H); 7.2-7.35 (m, 2H).

Step C: Preparation of 2-(3-(2,6-Difluorobenzyloxy)phenyl)acetic acid

To a stirred solution Ethyl 2-(3-(2,6-difluorobenzyloxy)phenyl)acetate (Step B, 7.86 g, 24 mmol) in absolute ethanol (120 ml) was added 1N NaOH (50 ml) at room temperature. The reaction mixture was stirred for 3 hours, or until all the starting material is gone, concentrated and diluted with chloroform and washed with 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 3.6 (s, 2H); 5.1 (s, 2H); 6.9 (m, 5H); 7.2-7.35 (m, 2H).

Example 11

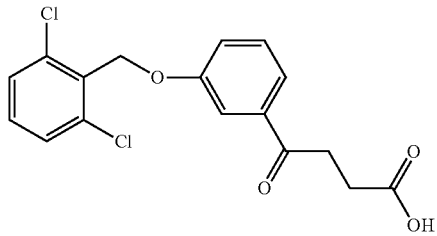 [SMILES: O=C(O)CCC(=O)c1cccc(OCc2c(Cl)cccc2Cl)c1]

4-(3-(2,6-Dichlorobenzyloxy)phenyl)-4-oxobutanoic acid

Step A: Preparation of 4-(2,6-Dichlorobenzyloxy)acetophenone

A solution of 2,6-Dichlorolbenzyl alcohol (15 g, 84.7 mmol) and diisopropyl azodicarboxylate (DIAD, 18.66 g, 92.2 mmol) in THF (50 ml) was added drop wise to a solution of 3-Hydroxyacetophenone (11.53 g, 84.7 mmol) and triphenylphosphine (24.22 g, 92.3 mmol) in THF (200 ml) at 0° C. The reaction mixture was stirred at room temperature for 4 hours, diluted with ether and washed with water, 1N NaOH and brine. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 2.5 (s, 3H); 5.3 (s, 2H); 7.2-7.3 (m, 2H); 7.4 (m, 3H); 7.6 (m, 2H).

Step B: Preparation of Ethyl 4-(3-(2,6-Dichlorobenzyloxy)phenyl)-4-oxobutanoate

To a stirred solution of 4-(2,6-Dichlorobenzyloxy)acetophenone (Step A, 12 g, 40.6 mmol) in dry THF (100 ml) and DMPU (30 ml) was added a solution of lithium bis(trimethylsilyl)amide (1M in THF, 47.21 ml) at –65° C. under argon. After 10 minutes of stirring at –65° C., ethyl bromoacetate (10.18 g, 61 mmol) was added rapidly. The reaction mixture was stirred for an additional 10 minutes and then warmed to room temperature for 4 hours. The crude mixture was taken in ethyl acetate and washed with water and brine. The aqueous layer was extracted one more time with ethyl acetate. The combined organic layers were dried over Na$_2$SO$_4$, filtered, concentrated and purified by flash chromatography on a silica gel column (ethyl acetate:hexane, 1:4) to provide the title compound.

$^1$H NMR (270 MHz, CDCl$_3$): 1.2 (t, 3H); 2.8 (t, 2H); 3.3 (t, 2H); 4.4 (q, 2H); 5.3 (s, 2H); 7.2-7.3 (m, 2H); 7.4 (m, 3H); 7.6 (m, 2H).

Step C: Preparation of 4-(3-(2,6-Dichlorobenzyloxy)phenyl)-4-oxobutanoic acid

A solution of Ethyl 4-(3-(2,6-Dichlorobenzyloxy)phenyl)-4-oxobutanoate (Step B, 14.86 g, 39 mmol) in abs ethanol (100 ml) was treated with 1N NaOH (60 ml) at room temperature. The reaction mixture was stirred for 3 hours, or until all the starting material is gone, concentrated and diluted with chloroform and washed with 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_1$): 2.8 (t, 2H); 3.3 (t, 2H); 5.3 (s, 2H); 7.2-7.3 (m, 2H); 7.4 (m, 3H); 7.6 (m, 2H).

Example 12

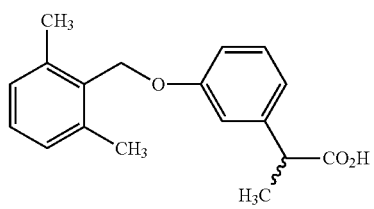 [SMILES: Cc1cccc(C)c1COc1cccc(C(C)C(=O)O)c1]

2-(3-(2,6-Dimethylbenzyloxy)phenyl)propanoic acid

Step A: Preparation of Ethyl 2-(3-(2,6-dimethylbenzyloxy)phenyl)acetate

A solution of 2,6-Dimethylbenzyl alcohol (5.25 g, 38.6 mmol) and diisopropyl azodicarboxylate (DIAD, 8.49 g, 42 mmol) in THF (30 ml) was added drop wise to a solution of Ethyl 3-hydroxyphenylacetate (6.66 g, 37 mmol) and triphenylphosphine (11 g, 42 mmol) in THF (100 ml). The reaction mixture was stirred at room temperature for 4 hours, diluted with ether and washed with water and brine. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 1.2 (t, 3H); 2.3 (s, 6H); 3.5 (s, 2H); 4.1 (q, 2H); 5.1 (s, 2H); 6.9 (m, 2H); 7.15-7.35 (m, 5H).

Step B: Preparation of Ethyl 4-(3-(2,6-dimethylbenzyloxy)phenyl)propanoate

To a stirred solution of Ethyl 2-(3-(2,6-dimethylbenzyloxy)phenyl)acetate (Step A, 6.35 g, 21.3 mmol) in dry THF (100 ml) was added a solution of lithium bis(trimethylsilyl)amide (1.0 M in THF, 31.91 ml) at –65° C. under argon. After 10 minutes of stirring at –65° C., iodomethane (15.12 g, 106.5 mmol) was added rapidly. The reaction mixture was warmed to room temperature for 6 hours. The crude mixture was taken in ethyl acetate and washed with water (2×). The aqueous layer was extracted one more time with ethyl acetate. The combined organic layers were washed with brine, dried over Na$_2$SO$_4$, filtered, concentrated and purified by flash chromatography on a silica gel column (ether:hexane, 1:5) to provide the title compound.

$^1$H NMR (270 MHz, CDCl$_3$): 1.2 (t, 3H); 1.5 (m, 3H); 2.4 (s, 6H); 3.7 (m, 1H); 4.1 (q, 2H); 5.1 (s, 2H); 6.9 (m, 2H); 7.15-7.35 (m, 5H).

Step C: Preparation of 4-(3-(2,6-dimethylbenzyloxy)phenyl)propanoic acid

A solution of Ethyl 4-(3-(2,6-dimethylbenzyloxy)phenyl)propanoate (Step B, 1.30 g, 4.2 mmol) in abs ethanol (30 ml) was treated with 1N NaOH (10 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 1.5 (m, 3H); 2.4 (s, 6H); 3.7 (m, 1H); 5.1 (s, 2H); 6.9 (m, 2H); 7.15-7.35 (m, 5H).

Example 13

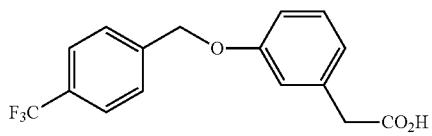 [SMILES: O=C(O)Cc1cccc(OCc2ccc(C(F)(F)F)cc2)c1]

2-(3-(4-(Trifluoromethyl)benzyloxy)phenyl)acetic acid

Step A: Preparation of Ethyl 2-(3-(4-(trifluoromethyl)benzyloxy)phenyl)acetate

To a stirred solution of Ethyl 2-(3-hydroxyphenyl)acetate (7.3 g, 30.5 mmol) in DMF (20 ml) was added potassium carbonate (5.47 g, 39.6 mmol) at room temperature followed by drop wise addition of 4-Trifluoromethylbenzyl bromide (6.04 g, 33.6 mmol). The reaction mixture was stirred for 12 hours and taken in ethyl acetate, washed with water (2×), brine, dried over Na$_2$SO$_4$, filtered, concentrated and purified by flash chromatography on a silica gel column (hex:ether 5:1) to give the title compound.

$^1$H NMR (270 MHz, CDCl$_3$): 1.2 (t, 3H); 3.7 (s, 2H); 4.1 (q, 2H); 5.1 (s, 2H); 6.9 (m, 3H); 7.2 (t, 1H); 7.5-7.7 (m, 4H).

Step B: Preparation of 2-(3-(4-(Trifluoromethyl)benzyloxy)phenyl)acetic acid

To a stirred solution Ethyl 2-(3-(4-(trifluoromethyl)benzyloxy)phenyl)acetate (Step A, 6 g, 17.7 mmol) in absolute ethanol (70 ml) was added 1N NaOH (36 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 3.7 (s, 2H); 5.1 (s, 2H); 6.9 (m, 3H); 7.2 (t, 1H); 7.5-7.7 (m, 4H).

Example 14

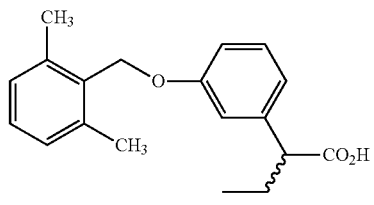 [SMILES: CCC(C(=O)O)c1cccc(OCc2c(C)cccc2C)c1]

2-(3-(2,6-Dimethylbenzyloxy)phenyl)butanoic acid

Step A: Preparation of Ethyl 2-(3-(2,6-dimethylbenzyloxy)phenyl)acetate

A solution of 2,6-Dimethylbenzyl alcohol (5.25 g, 38.6 mmol) and diisopropyl azodicarboxylate (DIAD, 8.49 g, 42 mmol) in THF (30 ml) was added drop wise to a solution of Ethyl 3-hydroxyphenylacetate (6.66 g, 37 mmol) and triphenylphosphine (11 g, 42 mmol) in THF (100 ml). The reaction mixture was stirred at room temperature for 4 hours, diluted with ether and washed with water and brine. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 1.2 (t, 3H); 2.3 (s, 6H); 3.5 (s, 2H); 4.1 (q, 2H); 5.1 (s, 2H); 6.9 (m, 2H); 7.15-7.35 (m, 5H).

Step B: Preparation of Ethyl 4-(3-(2,6-dimethylbenzyloxy)phenyl)butanoate

To a stirred solution of Ethyl 2-(3-(2,6-dimethylbenzyloxy)phenyl)acetate (Step A, 4.79 g, 16.0 mmol) in dry THF (60 ml) was added drop wise a solution of lithium diisopropylamide (1.0 M in THF, 25 ml) at −78° C. under argon followed by addition of hexamethylphosphoramide (HMPA, 15 ml). After 15 minutes of stirring at −78° C., Iodoethane (12.53 g, 80.3 mmol) was added rapidly. The reaction mixture was warmed to room temperature for 16 hours. The crude mixture was quenched with sat. NH$_4$Cl and extracted with ether (2×). The combined organic layers were washed with brine, dried over Na$_2$SO$_4$, filtered, concentrated and purified by flash chromatography on a silica gel column (ethyl acetate: hexane, 1:4) to provide the title compound.

$^1$H NMR (270 MHz, CDCl$_3$): 1.0 (t, 3H); 1.2 (m, 3H); 1.8 (m, 1H); 2.1 (m, 1H); 2.4 (s, 6H); 3.4 (m, 1H); 4.1 (q, 2H); 5.1 (s, 2H); 6.9 (m, 2H); 7.15-7.35 (m, 5H).

Step C: Preparation of 4-(3-(2,6-Dimethylbenzyloxy)phenyl)butanoic acid

A solution of Ethyl 4-(3-(2,6-dimethylbenzyloxy)phenyl) butanoate (Step B, 3.26 g, 10 mmol) in abs ethanol (60 ml) was treated with 1N NaOH (20 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 1.0 (t, 3H); 1.8 (m, 1H); 2.1 (m, 1H); 2.4 (s, 6H); 3.4 (m, 1H); 5.1 (s, 2H); 6.9 (m, 2H); 7.15-7.35 (m, 5H).

Example 15

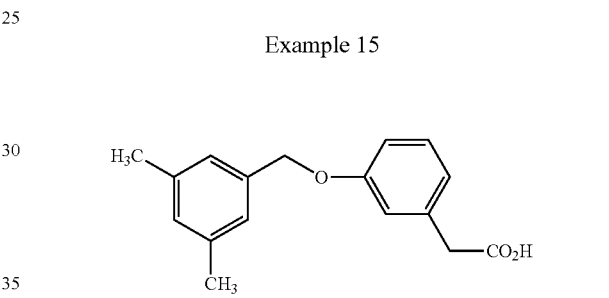

2-(3-(3,5-Dimethylbenzyloxy)phenyl)acetic acid

Step A: Preparation of Ethyl 2-(3-(3,5-dimethylbenzyloxy)phenyl)acetate

To a stirred solution of Ethyl 2-(3-hydroxyphenyl)acetate (3 g, 16.6 mmol) in DMF (20 ml) was added potassium carbonate (2.99 g, 21.6 mmol) at room temperature followed by drop wise addition of 3,5-Dimethylbenzyl bromide (3.30 g, 16.6 mmol). The reaction mixture was stirred for 16 hours and taken in ethyl acetate, washed with water (2×), brine, dried over Na$_2$SO$_4$, filtered, concentrated and purified by flash chromatography on a silica gel column (hex:ethyl acetate 4:1) to give the title compound.

Step B: Preparation of 2-(3-(3,5-Dimethylbenzyloxy)phenyl)acetic acid

To a stirred solution Ethyl 2-(3-(3,5-dimethylbenzyloxy) phenyl)acetate (Step A, 2.38 g, 8.0 mmol) in absolute ethanol (40 ml) was added 1N NaOH (16 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (400 MHz, CDCl$_3$): 2.4 (s, 6H); 3.7 (s, 2H); 5.1 (s, 2H); 6.9 (m, 3H); 7.2 (s, 1H); 7.25-7.35 (m, 3H).

Example 16

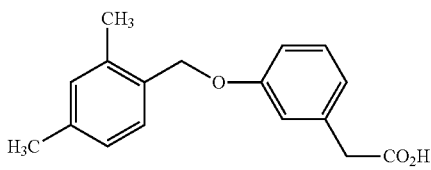 [SMILES: Cc1ccc(COc2cccc(CC(=O)O)c2)c(C)c1]

2-(3-(2,4-Dimethylbenzyloxy)phenyl)acetic acid

Step A: Preparation of Ethyl 2-(3-(2,4-dimethylbenzyloxy)phenyl)acetate

To a stirred solution of Ethyl 2-(3-hydroxyphenyl)acetate (3 g, 16.6 mmol) in DMF (20 ml) was added potassium carbonate (2.99 g, 21.6 mmol) at room temperature followed by drop wise addition of 2,4-Dimethylbenzyl chloride (3.11 g, 18.3 mmol). The reaction mixture was stirred for 16 hours and taken in ethyl acetate, washed with water (2×), brine, dried over Na$_2$SO$_4$, filtered, concentrated and purified by flash chromatography on a silica gel column (hex:ethyl acetate 4:1) to give the title compound.

Step B: Preparation of 2-(3-(2,4-Dimethylbenzyloxy)phenyl)acetic acid

To a stirred solution Ethyl 2-(3-(2,4-dimethylbenzyloxy) phenyl)acetate (Step A, 0.900 g, 3.0 mmol) in absolute ethanol (25 ml) was added 1N NaOH (10 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (400 MHz, CDCl$_3$): 2.4 (s, 6H); 3.6 (s, 2H); 5.1 (s, 2H); 6.9 (m, 3H); 7.25-7.35 (m, 4H).

Example 17

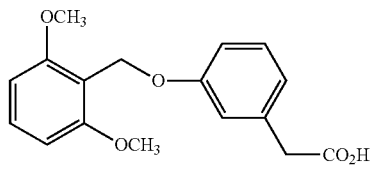

2-(3-(2,6-Dimethoxybenzyloxy)phenyl)acetic acid

Step A: Preparation of Ethyl 2-(3-(2,6-Dimethoxybenzyloxy)phenyl)acetate

A solution of 2,6-Dimethoxybenzyl alcohol (3.33 g, 19.8 mmol) and diisopropyl azodicarboxylate (DIAD, 4.36 g, 21.6 mmol) in THF (30 ml) was added drop wise to a solution of Ethyl 2-(3-hydroxyphenyl)acetate (4 g, 22.2 mmol) and triphenylphosphine (5.66 g, 21.6 mmol) in THF (80 ml). The reaction mixture was stirred at room temperature for 8 hours, diluted with ether and washed with water and brine. The organic layer was dried over Na$_2$SO$_4$, filtered, concentrated, and purified by flash chromatography on a silica gel column (hex:ethyl acetate 4:1) to give the title compound.

Step B: Preparation of 2-(3-(2,6-Dimethoxybenzyloxy)phenyl)acetic acid

To a stirred solution Ethyl 2-(3-(2,6-Dimethoxybenzyloxy)phenyl)acetate (Step A, 6 g, 18.2 mmol) in absolute ethanol (100 ml) was added 1N NaOH (40 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (400 MHz, CDCl$_3$): 3.7 (s, 2H); 3.8 (s, 6H); 5.1 (s, 2H); 6.5 (d, 2H); 6.8-7.1 (m, 3H); 7.2 (d, 1H); 7.3 (t, 1H).

Example 18

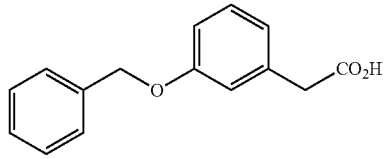 [SMILES: O=C(O)Cc1cccc(OCc2ccccc2)c1]

2-(3-(Benzyloxy)phenyl)acetic acid

Step A: Preparation of Ethyl 2-(3-(benzyloxy)phenyl)acetate

To a stirred solution of Ethyl 2-(3-hydroxyphenyl)acetate (3 g, 16.6 mmol) in DMF (25 ml) was added potassium carbonate (2.99 g, 21.6 mmol) at room temperature followed by drop wise addition of benzyl bromide (3.13 g, 18.3 mmol). The reaction mixture was stirred for 16 hours and taken in ethyl acetate, washed with water (2×) and brine. The organic layer was dried over Na$_2$SO$_4$, filtered, concentrated and purified by flash chromatography on a silica gel column (hex: ethyl acetate 4:1) to give the title compound.

Step B: Preparation of 2-(3-(Benzyloxy)phenyl)acetic acid

To a stirred solution Ethyl 2-(3-(benzyloxy)phenyl)acetate (Step A, 5.00 g, 18.5 mmol) in absolute ethanol (100 ml) was added 1N NaOH (40 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (400 MHz, CDCl$_3$): 3.6 (s, 2H); 5.1 (s, 2H); 6.8 (m, 2H); 7.1 (s, 1H), 7.2 (t, 1H), 7.35-7.45 (m, 5H).

Example 19

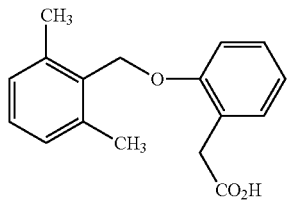 [SMILES: Cc1cccc(C)c1COc1ccccc1CC(=O)O]

2-(2-(2,6-Dimethylbenzyloxy)phenyl)acetic acid

Step A: Preparation of Ethyl 2-(2-hydroxyphenyl)acetate

The stirred solution of 2-(2-Hydroxyphenyl)acetic acid (10 g, 65.7 mmol) and p-Toluenesulfonic acid monohydrate (1.40 g, 7.3 mmol) in abs ethanol (100 ml) was refluxed for 4 hours or until all the starting material is consumed. The reaction mixture was concentrated, diluted with ethyl acetate and washed with 1M HCl and brine. The organic layer was dried over Na$_2$SO$_4$, filtered, concentrated, and purified by flash chromatography on a silica gel column (hex:ethyl acetate 2:1) to give the title compound.

Step B: Preparation of Ethyl 2-(2-(2,6-dimethylbenzyloxy)phenyl)acetate

A solution of 2,6-Dimethylbenzyl alcohol (2.72 g, 19.9 mmol) and diisopropyl azodicarboxylate (DIAD, 3.67 g, 18.2 mmol) in THF (30 ml) was added drop wise to a solution of Ethyl 2-(2-hydroxyphenyl)acetate (3 g, 16.6 mmol) and triphenylphosphine (4.76 g, 18.2 mmol) in THF (80 ml). The reaction mixture was stirred at room temperature for 6 hours, diluted with ether and washed with water and brine. The organic layer was dried over Na$_2$SO$_4$, filtered, concentrated, and purified by flash chromatography on a silica gel column (hex:ethyl acetate 4:1) to give the title compound.

Step C: Preparation of 2-(2-(2,6-Dimethylbenzyloxy)phenyl)acetic acid

To a stirred solution Ethyl 2-(2-(2,6-dimethylbenzyloxy) phenyl)acetate (Step B, 4.70 g, 15.7 mmol) in absolute ethanol (75 ml) was added 1N NaOH (35 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (400 MHz, CDCl$_3$): 2.35 (s, 6H); 3.6 (s, 2H); 5.1 (s, 2H); 7.0 (t, 1H); 7.1 (s, 1H), 7.2-7.25 (m, 2H), 7.30-7.35 (m, 2H); 7.4 (t, 1H).

What is claimed is:

1. A method of reducing the uric acid concentration in blood of, or increasing uric acid excretion from, a mammalian subject, comprising administering to the subject a compound 2-(3-(2,6-Dimethylbenzyloxy)-4-methylphenyl)acetic acid or a pharmaceutically acceptable salt thereof in an amount effective to reduce the uric acid concentration in blood of, or increase uric acid excretion from, the subject.

2. The method of claim 1, wherein the subject has a condition selected from the group consisting of gout, hyperuricemia, elevated levels of uric acid that do not meet the levels customarily justifying a diagnosis of hyperuricemia, renal dysfunction, kidney stones, cardiovascular disease, tumor-lysis syndrome, cognitive impairment, and early-onset essential hypertension.

3. The method of claim 1, wherein the subject is a human.

4. The method of claim 1, further comprising administering to the subject one or more other uric acid lowering drugs in a combined amount effective to reduce the uric acid concentration in blood of, or increase uric acid excretion from, the subject.

5. The method of claim 4, wherein the other uric acid lowering drug is selected from the group consisting of a xanthine oxidase inhibitor, a uricosuric agent, a urate transporter-1 inhibitor, a uricase, and a statin.

6. The method of claim 4, wherein the other uric acid lowering drug is administered in an amount that is less than the usual therapeutic dose when administered alone.

7. The method of claim 4, wherein the Compound or salt thereof and the one or more other uric acid lowering drugs are mixed together to form an admixture and the admixture is administered to the subject.

8. The method of claim 4, wherein the Compound or salt thereof and the one or more other uric acid lowering drugs are not mixed together to form an admixture but are administered independently to the subject.

9. The method of claim 1, wherein the Compound or salt thereof is formulated for oral administration.

10. 2-(3-(2,6-Dimethylbenzyloxy)-4-methylphenyl)acetic acid, or a pharmaceutically acceptable salt thereof.

* * * * *